United States Patent
Potts et al.

(10) Patent No.: US 11,812,227 B2
(45) Date of Patent: Nov. 7, 2023

(54) FOCUSING METHODS FOR A PROSTHESIS

(71) Applicant: Cochlear Limited, Macquarie University (AU)

(72) Inventors: Wendy Potts, Macquarie University (AU); Sara Ingrid Duran, Macquarie University (AU); Zachary Mark Smith, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 232 days.

(21) Appl. No.: 17/269,048

(22) PCT Filed: Nov. 15, 2019

(86) PCT No.: PCT/IB2019/059839
§ 371 (c)(1),
(2) Date: Feb. 17, 2021

(87) PCT Pub. No.: WO2020/100107
PCT Pub. Date: May 22, 2020

(65) Prior Publication Data
US 2021/0281961 A1 Sep. 9, 2021

Related U.S. Application Data

(60) Provisional application No. 62/768,371, filed on Nov. 16, 2018.

(51) Int. Cl.
*H04R 25/00* (2006.01)
(52) U.S. Cl.
CPC .................. *H04R 25/70* (2013.01)

(58) Field of Classification Search
CPC ....................................................... H04R 25/70
(Continued)

(56) References Cited

U.S. PATENT DOCUMENTS

| 9,095,708 B2 | 8/2015 | Carter |
| 2003/0105504 A1 | 6/2003 | Zierhofer |

(Continued)

FOREIGN PATENT DOCUMENTS

| EP | 2726017 B1 * | 11/2017 | .......... H04R 25/305 |
| KR | 101543814 B1 | 8/2015 | |

(Continued)

OTHER PUBLICATIONS

Extended European search report for European Patent Application No. 19 884 863.2, dated Jul. 6, 2022.
(Continued)

*Primary Examiner* — Sean H Nguyen
(74) *Attorney, Agent, or Firm* — Pilloff Passino & Cosenza LLP; Martin J. Cosenza

(57) ABSTRACT

A method of at least partially fitting a hearing prosthesis device to a recipient, including obtaining access to a sensory prosthesis that has been used to evoke a sensory percept using a first focusing regime for a temporal period corresponding to at least acclimation to the first focusing regime and adjusting a control setting of the prosthesis to increase focusing relative to that which is the case with respect to the first focusing regime, wherein the action of adjusting the control setting includes purposely adjusting the control setting to have focusing that is effectively less focused than a maximum focus possible.

20 Claims, 20 Drawing Sheets

(58) Field of Classification Search
USPC .......................................................... 381/60
See application file for complete search history.

(56) References Cited

U.S. PATENT DOCUMENTS

| | | |
|---|---|---|
| 2009/0240307 A1 | 9/2009 | Seligman |
| 2010/0145411 A1 | 6/2010 | Spitzer |
| 2010/0198301 A1 | 8/2010 | Smith |
| 2012/0116480 A1 | 5/2012 | Tsay et al. |
| 2014/0275730 A1 | 9/2014 | Lievens et al. |
| 2015/0343217 A1 | 12/2015 | Smith |
| 2016/0228704 A1 | 8/2016 | McLaughlin et al. |
| 2016/0279021 A1 | 9/2016 | Hyde et al. |
| 2016/0279413 A1* | 9/2016 | Schleich ................ H04R 25/70 |
| 2017/0001006 A1 | 1/2017 | Meister et al. |
| 2017/0224992 A1 | 8/2017 | Kulkarni et al. |
| 2017/0347209 A1* | 11/2017 | Heasman ............. H04R 25/305 |
| 2018/0110982 A1* | 4/2018 | Heasman ............. A61N 1/0541 |

FOREIGN PATENT DOCUMENTS

| | | | |
|---|---|---|---|
| KR | 20170042545 A | 4/2017 | |
| KR | 20170132277 A | 12/2017 | |

OTHER PUBLICATIONS

International Search Report & Written Opinion for PCT/IB2019/059839, dated Apr. 21, 2020.

\* cited by examiner

| A | B | C |
|---|---|---|
| α = 0.50 | C = 60 CL | T = 30 CL |
| α = 0.75 | C = 63 CL | T = X CL |
| α = 0.75 | C = 63 CL | T = 34 CL |
| α = 0.75 | C = 30 CL | T = 17 CL |
| α = 0.75 | C = 54 CL | T = 32 CL |
| α = 0.75 | C = 63 CL | T = 32 CL |

FIG. 12A

FOCUSING METHODS FOR A PROSTHESIS

CROSS-REFERENCE TO RELATED APPLICATIONS

This application claims priority to U.S. Provisional Application No. 62/768,371, entitled FOCUSING METHODS FOR A PROSTHESIS, filed on Nov. 16, 2018, naming Wendy POTTS of Centennial, Colo. as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant. Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound. In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound. Many devices, such as medical devices that interface with a recipient, have structural and/or functional features where there is utilitarian value in adjusting such features for an individual recipient. The process by which a device that interfaces with or otherwise is used by the recipient is tailored or customized or otherwise adjusted for the specific needs or specific wants or specific characteristics of the recipient is commonly referred to as fitting. One type of medical device where there is utilitarian value in fitting such to an individual recipient is the above-noted cochlear implant.

SUMMARY

In an exemplary embodiment, there is a method of at least partially fitting a hearing prosthesis device to a recipient, comprising obtaining access to a sensory prosthesis that has been used to evoke a sensory percept using a first focusing regime for a temporal period corresponding to at least acclimation to the first focusing regime, and adjusting a control setting of the prosthesis to increase focusing relative to that which is the case with respect to the first focusing regime, wherein the action of adjusting the control setting includes purposely adjusting the control setting to have focusing that is effectively less focused than a maximum focus possible.

In an exemplary embodiment, there is a system for at least partially fitting a prosthesis to a recipient, comprising a device configured to control stimulation to evoke a sensory percept using the prosthesis, and a device configured to enable the recipient to make adjustments of focusing of the prosthesis with respect to tissue stimulation.

In an exemplary embodiment, there is a non-transitory computer-readable media having recorded thereon, a computer program for executing at least a portion of a method of fitting a sensory prosthesis to a recipient, the computer program including code for enabling recipient controlled gradual transitioning of the prosthesis from less focused stimulation to more focused stimulation.

In an exemplary embodiment, there is a method, comprising adjusting and/or changing control settings of a sensory prosthesis in an incremental manner, wherein the action of adjusting and/or changing the control settings in the incremental manner reduces the risk of overstimulation of the recipient relative to that which would be the case in the absence of the limitation of the incremental manner.

BRIEF DESCRIPTION OF THE DRAWINGS

Embodiments are described below with reference to the attached drawings, in which:

FIG. 12A presents exemplary conceptual data blocks for maps that change according to teachings herein;

DETAILED DESCRIPTION

Embodiments will be described in terms of a cochlear implant, but it is to be noted that the teachings detailed herein can be applicable to other types of hearing prostheses, and other types of sensory prostheses as well, such as, for example, retinal implants, etc. In an exemplary embodiment of a cochlear implant and an exemplary embodiment of system that utilizes a cochlear implant with other components will first be described, where the implant and the system can be utilized to implement at least some of the teachings detailed herein. In an exemplary embodiment, any disclosure herein of a microphone or other sound capture device and a device that evokes a hearing percept corresponds to a disclosure of an alternate embodiment where the microphone or other sound capture device is replaced with an optical sensing device and the device that evokes a hearing percept is replaced with a device that evokes a sight percept (e.g., again, the components of a retinal implant, for example).

Figure 1:
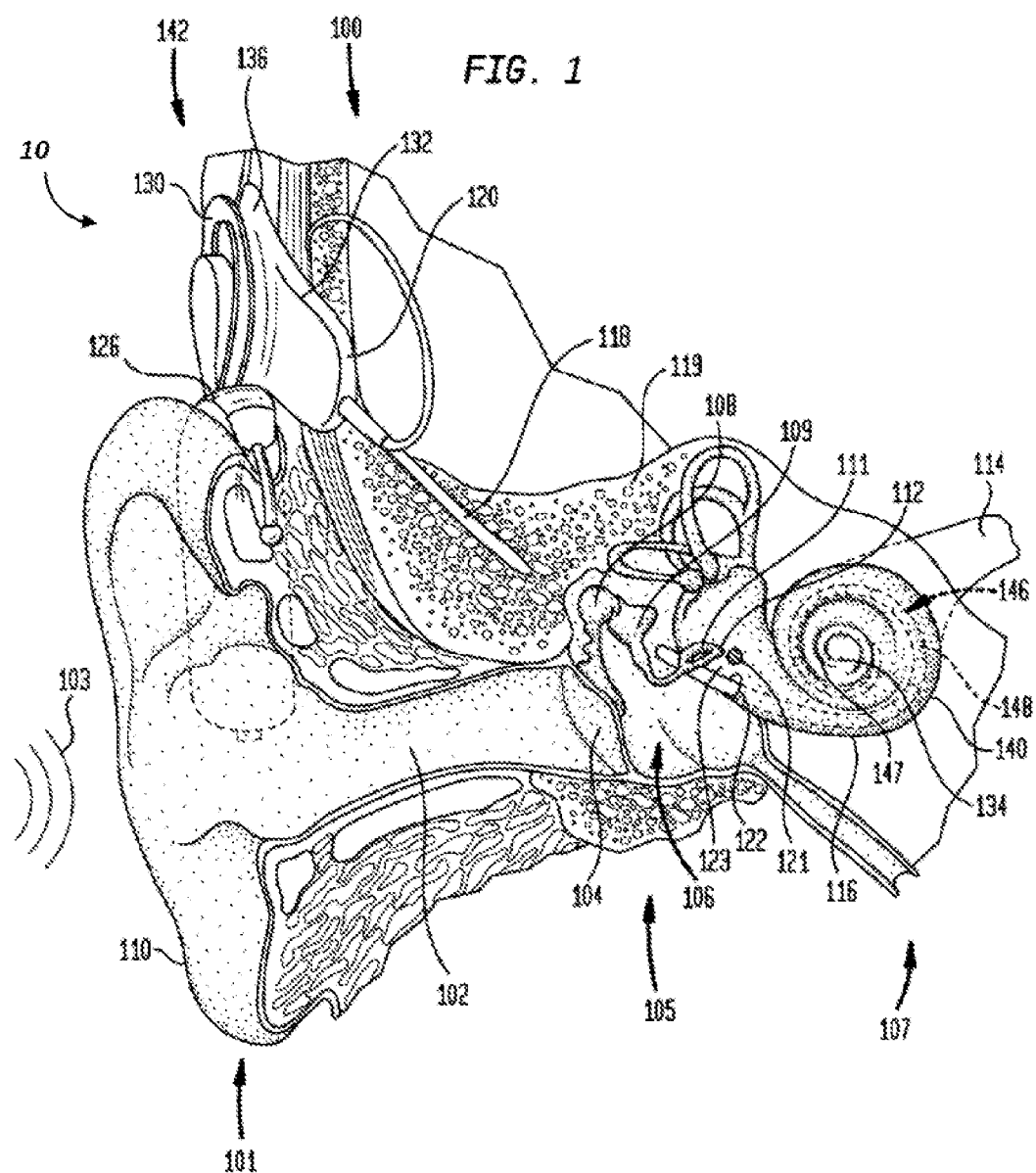
FIG. 1 is a perspective view of an exemplary hearing prosthesis in which at least some of the teachings detailed herein are applicable.

FIG. 1 is a perspective view of a cochlear implant, referred to as cochlear implant 100, implanted in a recipient, to which some embodiments detailed herein and/or variations thereof are applicable. The cochlear implant 100 is part of a system 10 that can include external components in some embodiments, as will be detailed below. Additionally, it is noted that the teachings detailed herein are also applicable to other types of hearing prostheses, such as by way of example only and not by way of limitation, bone conduction devices (percutaneous, active transcutaneous and/or passive transcutaneous), direct acoustic cochlear stimulators, middle ear implants, and conventional hearing aids, etc. Indeed, it is noted that the teachings detailed herein are also applicable to so-called multi-mode devices. In an exemplary embodiment, these multi-mode devices apply both electrical stimulation and acoustic stimulation to the recipient. In an exemplary embodiment, these multi-mode devices evoke a hearing percept via electrical hearing and bone conduction hearing. Accordingly, any disclosure herein with regard to one of these types of hearing prostheses corresponds to a disclosure of another of these types of hearing prostheses, or any medical device for that matter, unless otherwise specified, or unless the disclosure thereof is incompatible with a given device based on the current state of technology. Thus, the teachings detailed herein are applicable, in at least some embodiments, to partially implantable and/or totally implantable medical devices that provide a wide range of therapeutic benefits to recipients, patients, or other users, including hearing implants having an implanted microphone, auditory brain stimulators, visual prostheses (e.g., bionic eyes), sensors, etc.

In view of the above, it is to be understood that at least some embodiments detailed herein and/or variations thereof are directed towards a body-worn sensory supplement medical device (e.g., the hearing prosthesis of FIG. 1, which supplements the hearing sense, even in instances when there are no natural hearing capabilities, for example, due to degeneration of previous natural hearing capability or to the lack of any natural hearing capability, for example, from birth). It is noted that at least some exemplary embodiments of some sensory supplement medical devices are directed towards devices such as conventional hearing aids, which supplement the hearing sense in instances where some natural hearing capabilities have been retained, and visual prostheses (both those that are applicable to recipients having some natural vision capabilities and to recipients having no natural vision capabilities). Accordingly, the teachings detailed herein are applicable to any type of sensory supplement medical device to which the teachings detailed herein are enabled for use therein in a utilitarian manner. In this regard, the phrase sensory supplement medical device refers to any device that functions to provide sensation to a recipient irrespective of whether the applicable natural sense is only partially impaired or completely impaired, or indeed never existed.

The recipient has an outer ear 101, a middle ear 105, and an inner ear 107. Components of outer ear 101, middle ear 105, and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109, and the stapes 111. Bones 108, 109, and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142, that is part of system 10 (along with cochlear implant 100), which, as described below, is configured to provide power to implant, where the implanted cochlear implant includes a battery that is recharged by the power provided from the external device 142.

In the illustrative arrangement of FIG. 1, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire.

Cochlear implant 100 further comprises a main implantable component 120 and an elongate electrode assembly 118. In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone in internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments, electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

Figure 2A:
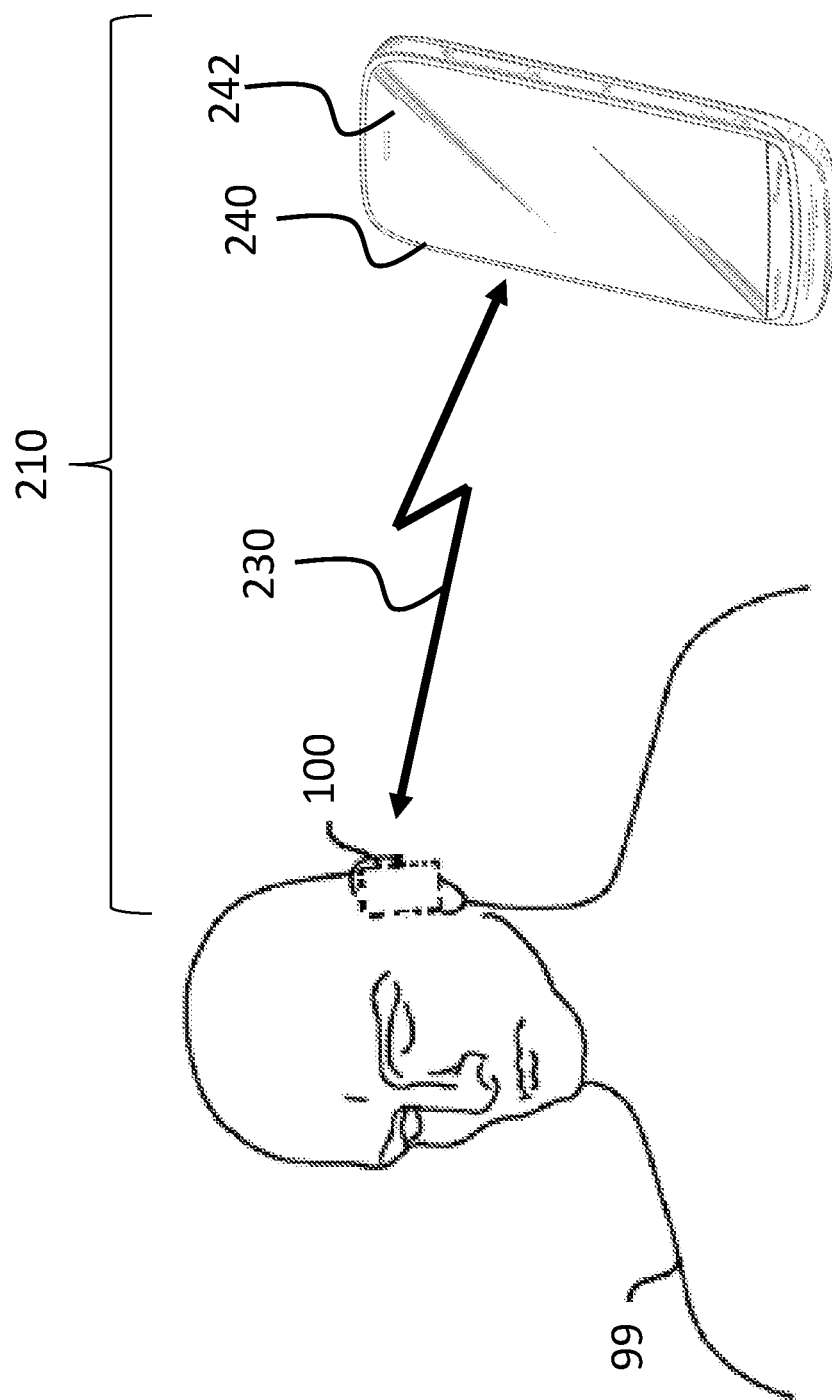
FIGS. 2A-2B presents exemplary systems.

FIG. 2A depicts an exemplary system 210 according to an exemplary embodiment, including hearing prosthesis 100, which, in an exemplary embodiment, corresponds to cochlear implant 100 detailed above, and a portable body carried device (e.g., a portable handheld device as seen in FIG. 2A, a watch, a pocket device, etc.) 240 in the form of a mobile computer having a display 242. The system includes a wireless link 230 between the portable handheld device 240 and the hearing prosthesis 100. In an embodiment, the prosthesis 100 is an implant implanted in recipient 99 (as represented functionally by the dashed lines of box 100 in FIG. 2A).

In an exemplary embodiment, the system 210 is configured such that the hearing prosthesis 100 and the portable handheld device 240 have a symbiotic relationship. In an exemplary embodiment, the symbiotic relationship is the ability to display data relating to, and, in at least some instances, the ability to control, one or more functionalities of the hearing prosthesis 100. In an exemplary embodiment, this can be achieved via the ability of the handheld device 240 to receive data from the hearing prosthesis 100 via the wireless link 230 (although in other exemplary embodiments, other types of links, such as by way of example, a wired link, can be utilized). As will also be detailed below, this can be achieved via communication with a geographically remote device in communication with the hearing prosthesis 100 and/or the portable handheld device 240 via link, such as by way of example only and not by way of limitation, an Internet connection or a cell phone connection. In some such exemplary embodiments, the system 210 can further include the geographically remote apparatus as well. Again, additional examples of this will be described in greater detail below.

As noted above, in an exemplary embodiment, the portable handheld device 240 comprises a mobile computer and a display 242. In an exemplary embodiment, the display 242 is a touchscreen display. In an exemplary embodiment, the portable handheld device 240 also has the functionality of a portable cellular telephone. In this regard, device 240 can be, by way of example only and not by way of limitation, a smart phone as that phrase is utilized generically. That is, in an exemplary embodiment, portable handheld device 240 comprises a smart phone, again as that term is utilized generically.

It is noted that in some other embodiments, the device 240 need not be a computer device, etc. It can be a lower tech recorder, or any device that can enable the teachings herein.

The phrase "mobile computer" entails a device configured to enable human-computer interaction, where the computer is expected to be transported away from a stationary location during normal use. Again, in an exemplary embodiment, the portable handheld device 240 is a smart phone as that term is generically utilized. However, in other embodiments, less sophisticated (or more sophisticated) mobile computing devices can be utilized to implement the teachings detailed herein and/or variations thereof. Any device, system, and/or method that can enable the teachings detailed herein and/or variations thereof to be practiced can be utilized in at least some embodiments. (As will be detailed below, in some instances, device 240 is not a mobile computer, but instead a remote device (remote from the hearing prosthesis 100. Some of these embodiments will be described below).)

In an exemplary embodiment, the portable handheld device 240 is configured to receive data from a hearing prosthesis and present an interface display on the display from among a plurality of different interface displays based on the received data. Exemplary embodiments will sometimes be described in terms of data received from the hearing prosthesis 100. However, it is noted that any disclosure that is also applicable to data sent to the hearing prostheses from the handheld device 240 is also encompassed by such disclosure, unless otherwise specified or otherwise incompatible with the pertinent technology (and vice versa).

It is noted that in some embodiments, the system 210 is configured such that cochlear implant 100 and the portable device 240 have a relationship. By way of example only and not by way of limitation, in an exemplary embodiment, the relationship is the ability of the device 240 to serve as a remote microphone for the prosthesis 100 via the wireless link 230. Thus, device 240 can be a remote mic. That said, in an alternate embodiment, the device 240 is a stand-alone recording/sound capture device.

It is noted that in at least some exemplary embodiments, the device 240 corresponds to an Apple Watch™ Series 1 or Series 2, as is available in the United States of America for commercial purchase as of Jun. 6, 2018. In an exemplary embodiment, the device 240 corresponds to a Samsung Galaxy Gear™ Gear 2, as is available in the United States of America for commercial purchase as of Jun. 6, 2018. The device is programmed and configured to communicate with the prosthesis and/or to function to enable the teachings detailed herein.

Figure 2B:
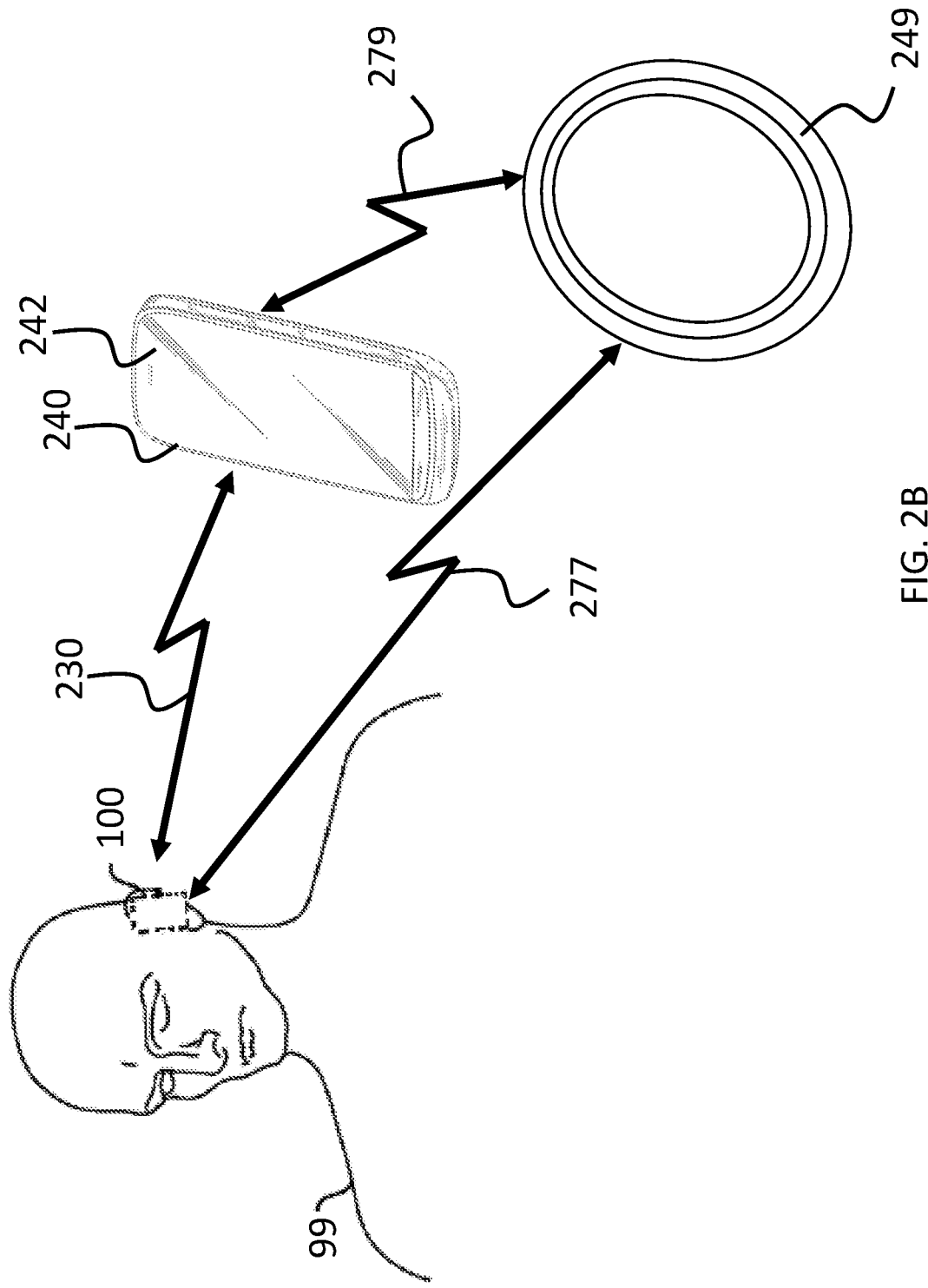

In an exemplary embodiment, a telecommunication infrastructure can be in communication with the hearing prosthesis 100 and/or the device 240. By way of example only and not by way of limitation, a telecoil 249 or some other communication system (Bluetooth, etc.) is used to communicate with the prosthesis and/or the remote device. FIG. 2B depicts an exemplary quasi-functional schematic depicting communication between an external communication system 249 (e.g., a telecoil), and the hearing prosthesis 100 and/or the handheld device 240 by way of links 277 and 279, respectively (note that FIG. 2B depicts two-way communication between the hearing prosthesis 100 and the external audio source 249, and between the handheld device and the external audio source 249—in alternate embodiments, the communication is only one way (e.g., from the external audio source 249 to the respective device)). In an exemplary embodiment, the device 240 has a test interface application thereon, as will be described in greater detail below.

Because the cochlea is tonotopically mapped (i.e., spatial locations that are responsive to stimulus signals in a particular frequency range are identified), frequencies may be allocated to one or more electrodes of the electrode assembly to generate an electric field in positions in the cochlea that are close to the region that would naturally be stimulated in normal hearing. This enables the prosthetic hearing implant to bypass the hair cells in the cochlea to directly deliver electrical stimulation to auditory nerve fibers, thereby allowing the brain to perceive hearing sensations resembling natural hearing sensations. In achieving this, processing channels of the sound processing unit of the BTE 126 (i.e., specific frequency bands with their associated signal processing paths), are mapped to a set of one or more electrodes to stimulate a desired nerve fiber or nerve region of the cochlea. Such sets of one or more electrodes for use in stimulation are referred to herein as "electrode channels" or "stimulation channels." In at least some exemplary embodiments, each channel has a "base" electrode corresponding to the electrode of the electrode array that is proximate the tonotopically mapped cochlea for a given frequency or frequency range.

Figure 2C:
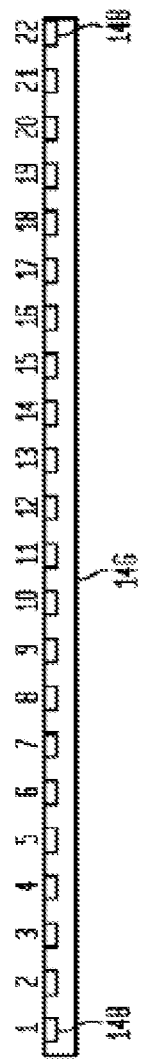
FIG. 2C presents an exemplary electrode array.

FIG. 2C illustrates a more detailed view, albeit functionally, of an exemplary electrode array 146 comprising a plurality of electrodes 148 labeled 1-22, in accordance with an embodiment. In an exemplary embodiment, each electrode 148 is an electrode that corresponds to a specific frequency band channel of the cochlear implant 100, where electrode 22 corresponds to the lowest frequency band (channel), and electrode 1 corresponds to the highest frequency band (channel), as will be discussed in greater detail below. Briefly, it is noted that during stimulation by the electrodes to evoke a hearing percept, one or more electrodes 148 is activated at a given electrode stimulation level (e.g., current level). This electrode stimulation level is pre-set during a fitting process. For example, in at least some instances, an audiologist adjusts stimulation channel electrode current levels of the cochlear implant 100 based on empirical data. More specifically, in at least some scenarios, stimulation channel electrode current levels are adjusted by an audiologist based on threshold and comfort levels. Then, in at least some scenarios, the cochlear implant 100 is configured such that respective stimulation channels of the cochlear implant 100 have those respective current levels. This can be done, for example, by programming the cochlear implant 100 or by any other process that sets the channels of the cochlear implant 100 to have the pertinent electrical stimulation levels. Any arrangement of the cochlear implant 100 and/or other equipment/devices that will enable the teachings detailed herein and/or variations thereof to be practiced can be used in at least some embodiments.

Figure 3:
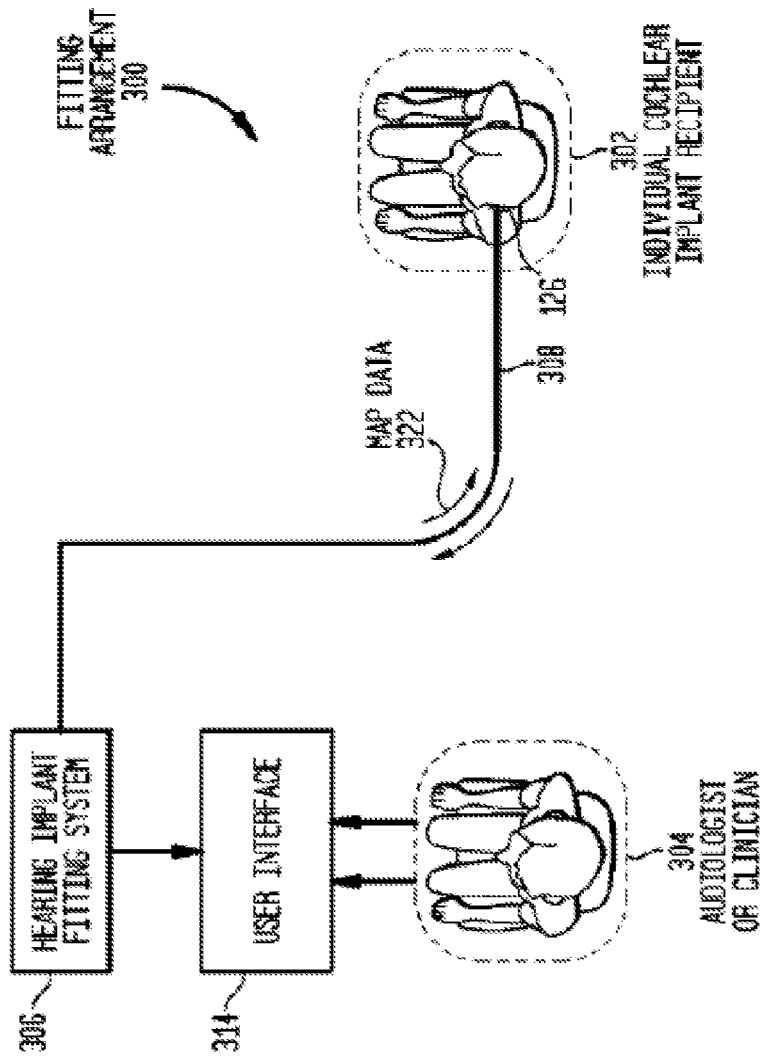
FIG. 3 presents an exemplary system.

FIG. 3 is a schematic diagram illustrating one exemplary arrangement 300 in which a hearing implant fitting system 306 may be used to fit a sensory prosthesis, such as a cochlear implant or a retinal implant (as would be modified to do so), in accordance with an embodiment. As shown in FIG. 3, an audiologist or clinician 304 may use a fitting system 306 ("fitting system" herein) comprising interactive software and computer hardware to create individualized recipient map data 322 that are digitally stored on system 306, and ultimately downloaded to the memory of the sound processing unit 126 for recipient 302. System 306 may be programmed and/or implement software programmed to carry out one or more of the functions of mapping, neural response measuring, acoustic stimulating, and recording of neural response measurements and other stimuli. (As will be detailed below, some embodiments do not use this system, but instead use the system 210 or a variation thereof—any disclosure herein associated with system 306 corresponds to a disclosure of such associated with system 210 and the variations thereof, unless otherwise noted. Also, any disclosure of a manual activity corresponds to a disclosure of an alternate embodiment where such is automated or semiautomated, and it is to be understood that system 210 is configured to be operated in such a manner.)

In the embodiment illustrated in FIG. 3, sound processing unit 126 of cochlear implant 100 may be connected directly to fitting system 306 to establish a data communication link 308 between the sound processing unit 126 and fitting system 306. System 306 is thereafter bi-directionally coupled by a data communication link 308 with sound processing unit 126. It should be appreciated that although sound processing unit 126 and fitting system 306 are connected via a cable in FIG. 3, any communications link now or later developed may be utilized to communicably couple the implant and fitting system.

Some exemplary embodiments will now be described. It is noted that in an exemplary embodiment, the system of FIG. 3 can be utilized in at least some of the teachings detailed below or otherwise to implement at least some of the teachings detailed below, while in other embodiments, the system is not necessarily utilized. It is noted that the following is but exemplary, and that alternative methods can be practiced utilizing other devices other than the fitting system 306 and/or alternative methods can be practiced to fit a prosthesis that is different than the cochlear implant.

Briefly, at least some teachings detailed herein and/or variations thereof are applicable to the development of a map for a cochlear implant user. As will be detailed herein, the teachings detailed herein and/or variations thereof can be applicable to other types of hearing prostheses other than a cochlear implant. Still further, the teachings detailed herein and/or variations thereof can be applicable in at least some embodiments to hybrid devices and bimodal devices that utilize the cochlear implant along with another type of hearing device (e.g., a traditional hearing aid).

More specifically, in at least some exemplary embodiments, there is an algorithm that enables the development, including the automatic development, of a new electrical output map such that the cochlear implant operates differently than that which was previously the case.

In at least some exemplary embodiments, the cochlear implant includes one or more MAPs stored therein. MAPs are programs that are used in combination with other components to control the input to the electrodes on the array that are implanted into the cochlea. In an exemplary embodiment, the cochlear implant is mapped. In an exemplary embodiment, the cochlear implant processor is connected to the audiologist's computer for MAPping. Using a series of "beeps," and measuring the CI user's response, the audiologist sets threshold (T) and loud but comfortable (C) levels for each electrode. The audiologist might also adjust the stimulation rate or programming strategy used for the MAP—these refer to the various computer algorithms and programs used to translate acoustic sound (what people with typical hearing perceive) into the correct combination of electrode stimulations to give the cochlear implant user that same sensation of sound. The finalized map is loaded into the cochlear implant or otherwise stored therein, and the recipient utilizes the cochlear implant with that map to evoke a hearing percept based on sound captured by the implant or otherwise provided to the implant via an audio signal.

The map can be adjusted or otherwise replaced during the temporal period extending after the initial mapping. By way of example only and not by way of limitation, in an exemplary scenario, the recipient can experience a fitting session with an audiologist or without an audiologist (e.g., using system 210, etc., as will be described below), where the cochlear implant is fitted to the recipient, and the map associated or otherwise that results from that fitting is stored into the cochlear implant. The recipient then goes on with life for a couple weeks or a couple of months and then returns to the audiologist to have the map adjusted or the map replaced with a new map. In some instances, the audiologist subjects the recipient to a series of tests or otherwise a series of measurements are taken of the recipient, and the data from those measurements is utilized to adjust the map or otherwise develop a new map. This adjusted map or otherwise developed new map is then loaded or otherwise stored in the cochlear implant, and the recipient than goes on with life until the next mapping session, etc. It is noted that any reference to adjusting the map herein corresponds to a disclosure of developing a new map, and vice versa, unless otherwise noted. It is also noted that the term "settings" will often be used herein. Any reference to developing or otherwise adjusting settings corresponds to a disclosure of adjusting or otherwise developing map data and vice versa unless otherwise noted.

In these fitting and/or mapping sessions, various measurements are taken of the recipient. Typically, these measurements are taken in coordination with stimulation applied to the recipient. Indeed, many of these measurements are measurements of physiological reactions that result from the applied stimulation. These measurements can be evaluated or otherwise used to determine adjustments to the map or otherwise develop new map settings.

As an initial matter, audiologist 304 (any action disclosed herein that is executed by an audiologist corresponds to a disclosure of an action that is executed an automated manner by any of the systems detailed herein unless otherwise noted providing the art enable such) may set up the cochlear implant system 100 and provide the cochlear implant system 100 with an initial set of parameters. This may involve calibrating the cochlear implant 100, as well as determining and setting the threshold and maximum comfortable levels for each stimulation channel of the electrode array 146. Additionally, during the initial set up, the audiologist may provide a set of default weights to be initially used for each of the stimulation channels. Note also that the results of these actions can be the development of the map that is utilized during a first temporal period in which, for example, a lower level of focus stimulation, such as monopolar stimulation for example, is utilized. It can be the temporal period during which time the recipient becomes acclimated to utilizing the cochlear implant with such focusing, after which the more refined focusing regimes are implemented in accordance with the teachings detailed below.

Figure 4:
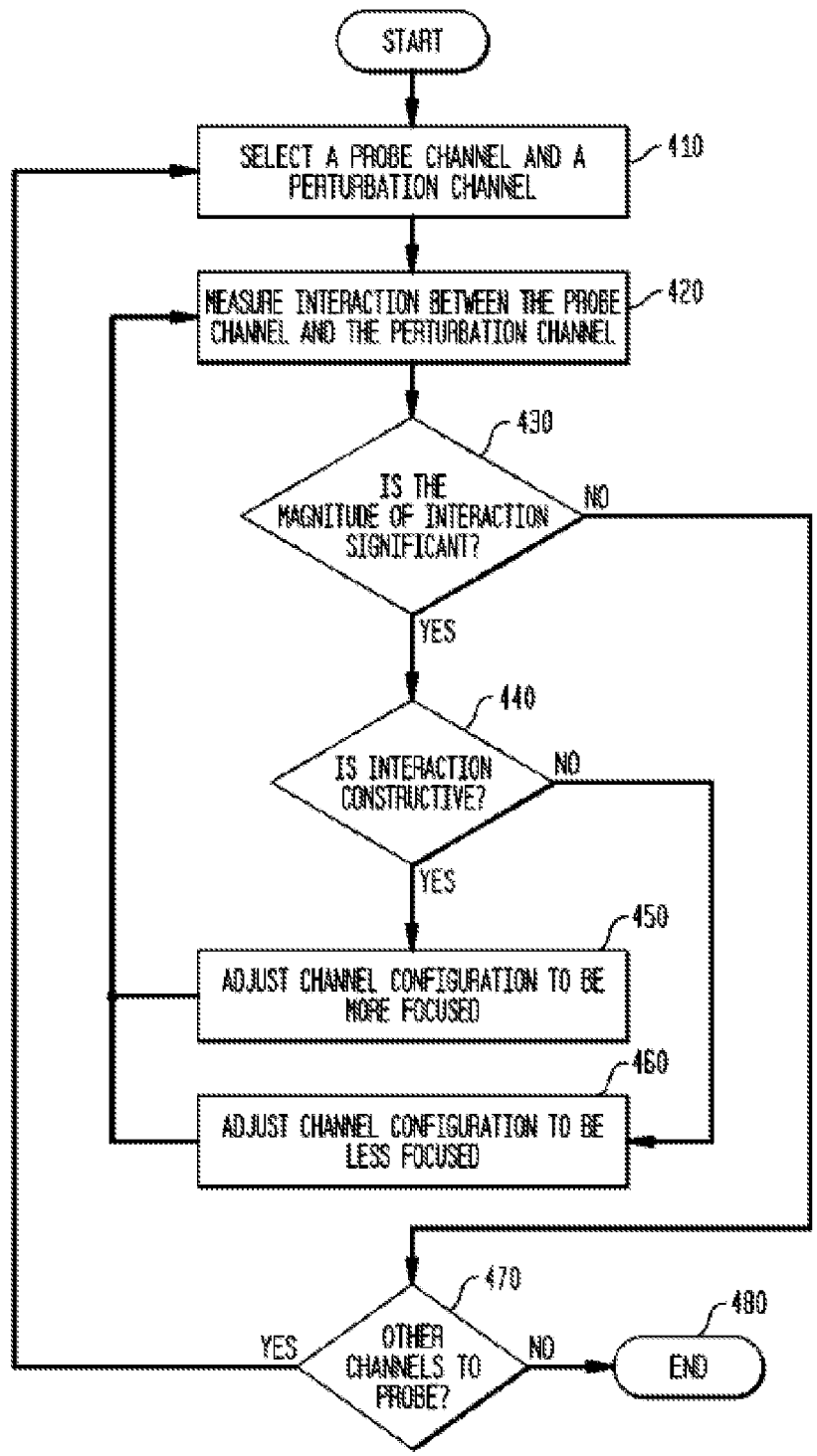
FIGS. 4 and 5 present flowcharts for exemplary algorithms.

FIG. 4 is a high-level flow chart illustrating operations that may be performed for adjusting complex stimulation channel weights, in accordance with an embodiment. FIG. 4 will be discussed with reference to the fitting system illustrated in FIG. 3. However, it should be noted that this is exemplary only and provided for explanatory purposes, and the general method of FIG. 4 may be used with other types of systems. Indeed, in an exemplary embodiment, the method of FIG. 4 is executed without audiologist interaction and/or is executed using, for example, device 240.

In the discussion below of FIGS. 3 and 4, the exemplary cochlear implant 100 will be assumed to include an electrode array comprising 22 electrodes plus an extra-cochlea electrode and providing 20 tripolar stimulation channels. However, it should be noted that this is exemplary only for explanatory purposes and the method of FIG. 4 may be used with other complex stimulation channels, such as phased-array stimulation channels. A more detailed description of how the process of FIG. 4 may be utilized to adjust the weights for phased-array stimulation channels will be provided below with reference to FIG. 7. Exemplary embodiments of cochlear implants include electrode arrays that are located in the cochlea that have 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 or more or any value or range of values therebetween in integer increments electrodes that are on the array and will be located in the cochlea.

These stimulation channels may be tripolar stimulation channels in which current flows from a center electrode (e.g., electrode 2) to its neighboring electrodes (e.g., electrodes 1 and 3) and an extra-cochlea electrode. In initially setting up the cochlear implant 100, audiologist 304 may use the fitting system 306 to assign a set of default weights to each of the electrodes for each stimulation channel, such as, for example, a weight of +1.0 to the center electrode, a weight of −0.3 to each of the neighboring electrodes and a weight of −0.4 to the extra-cochlea electrode, such that each of the neighboring electrodes (e.g., 1 and 3) sink 30% of the current and the extra-cochlea electrode sinks 40% of the current from the center electrode (e.g., 2).

After initially setting-up the cochlear implant system 100 with default weights for the stimulation channels, the process of FIG. 4 may be used to adjust the electrode weights for each stimulation channel to adjust the focus of the stimulation channel. It is noted that some of the teachings below include devices systems and/or methods that enable focusing to a maximum achievable value or otherwise to an optimized level. As will be described in greater detail below, at least some exemplary embodiments can include (but as with all embodiments, do not necessarily do so—other embodiments can use other methods/take other actions) developing maps and utilizing maps that have focusing at levels below the maximum and/or the optimum level. In this regard, the teachings detailed herein associated with evaluating the focusing vis-à-vis the probe and perturbation channels, for example, may not necessarily be implemented in all implementations and/or even in some implementations of the teachings detailed herein. The utilization of such can be for setting boundaries in at least some exemplary embodiments, but it is noted that some embodiments do not entail identifying or otherwise knowing those boundaries corollary to this is that in at least some exemplary embodiments, the boundaries could be determined at the beginning of a process, but are not again determined/redetermined after such.

First, for example, fitting system 306 and/or an application on device 240, etc., selects a probe channel and a perturbation channel from amongst the plurality of stimulation channels at block 410. In the exemplary 22 electrode array, the first stimulation channel (SC1) is centered at electrode 2 with the neighboring electrodes (1 and 3) and extra-cochlea electrode serving as the sink. This first stimulation channel (SC1) may be chosen as the probe channel. The perturbation channel is selected in this example to be a stimulation channel neighboring the selected probe channel. Thus, in this example, the perturbation channel is selected to be the second stimulation channel (SC2) centered at electrode 3. It should, however, be noted that any stimulation channel may be selected as the initial probe channel in the process of FIG. 4, and the first stimulation channel (SC1) was chosen simply for explanatory purposes. It should also be noted that in embodiments, the audiologist 304, using user interface 314, may select the probe and perturbation channels or override or the channels selected by the fitting system.

Next, fitting system 306 and/or an application on device 240, directs the cochlear implant to apply stimulation signals that are applied on the selected probe and perturbation channels and measures their interaction at block 420. Various methods and systems may be used for measuring the interaction between the probe and perturbation channels, and exemplary methods and systems will be discussed in more detail below.

After measuring the interaction between the probe and perturbation channels, the fitting system 306 and/or an application on device 240, checks to see if the magnitude of the interaction exceeds a threshold value at block 430. Additionally, in certain situations, the magnitude of the interaction might never fall below the specified threshold. Rather, the measured interaction may alternate between being constructive and destructive as the channel configurations are adjusted, but never drop below the threshold. In such a case, the fitting system 360 and/or an application on device 240, may stop the iterative process at block 430 at the point where the magnitude of the interaction is minimized (i.e., the point where the measured interaction alternates between constructive and destructive). In an embodiment, the measured interaction may be determined to be minimized when the magnitude of the measured interaction has not reduced after a pre-determined number of passes through block 430.

If the measured interaction is determined to exceed the threshold and is not determined to be minimized, the fitting system 306 and/or an application on device 240, determines whether the interaction between the probe and perturbation channels is constructive or destructive at block 440. As used herein, constructive interaction refers to a perturbation channel that constructively interferes with the probe channel to increase the magnitude of the electric field generated by the probe channel; and, destructive interaction refers to a perturbation channel that destructive interferes with the probe channel to decrease the magnitude of the electric field generated by the probe channel.

If the interaction is constructive, the fitting system 306 and/or an application on device 240, adjusts the weights for the probe channel and/or perturbation channel to increase the focus of the probe channel and/or perturbation channel at block 450 and provides the new weights to the cochlear implant 100. However, if the measured interaction is destructive, the fitting system 306 and/or an application on device 240, adjusts the weights for the probe channel and/or perturbation channel to decrease the focus of the probe channel and/or perturbation channel at block 460 and provides the new weights to cochlear implant 100. As used herein the term focus refers to the concentration of the electric field produced by the stimulation channel during stimulation of the implanted electrode array. For example, if the focus of the stimulation channel is increased, then the resulting electric field is narrowed. And, decreasing the focus of the stimulation channel refers to widening the resulting electric field.

After the weights are adjusted, the iterative process returns to block 410, where stimulations are applied using the new weights (block 410) and the interaction between the probe and perturbation channels with the updated weights is measured (block 420). This iterative process continues until the measured interaction between the probe and perturbation channels fall below the threshold at block 430. Once the measured interaction is below the threshold, the fitting system 306 next checks, at block 470, if there are additional stimulation channels that should be checked. If so, the process returns to step 410 and new stimulation channels are selected as the probe channel and the perturbation channel. For example, after adjusting the weights for stimulation channel 1 (SC1) as the probe channel, the process may then select stimulation channel 2 (SC2) as the probe channel to adjust the weights of stimulation channel 2 (SC2). As noted above, in embodiments, a neighboring stimulation channel is selected as the perturbation channel. As such, in this second pass through, the fitting system 306 may select either the first (SC1) or third (SC3) stimulation channel as the perturbation channel. The process may then be repeated for each stimulation channel until it is determined at block 470 that all stimulation channels for the cochlear implant 100 have been focused (i.e., had their weights adjusted). After which, the process ends at block 480.

As noted above, fitting system 306 and/or an application on device 240, at block 420 measures an interaction between the probe and perturbation channels. The following provides a more detailed explanation of an exemplary mechanism that may be employed for measuring the interaction. First, fitting system 306 and/or an application on device 240, may direct cochlear implant 100 to apply stimulation on the probe and perturbation channels using an identical waveform shape with the only exception being a difference in overall amplitude between the two waveforms.

The amplitude of the perturbation channel stimulation may be set to a level below the perturbation channel's threshold level, referred to herein as a sub-threshold level. As noted above, this threshold level may be determined during set-up of the cochlear implant 100 using fitting system 306 and/or an application on device 240. The threshold for the probe channel in the presence of the sub-threshold perturbation channel may then be determined using, for example, a verbal feedback methodology. For example, fitting system 306 and/or an application on device 240, may iteratively increase the level of the probe channel in the presence of the sub-threshold perturbation channel until the recipient indicates that they hear the probe channel.

Next, the polarity of the perturbation channel may be reversed and stimulation simultaneously applied on probe channel and perturbation channels. After determining the two probe threshold values (one with a perturbation channel with the same polarity and one with a perturbation channel with the opposite polarity), an interaction index (II) may be computed. This II may use the following formula:

$$II(\text{probe, pert}) = \frac{probeThreshold(\text{opposite}) - probeThreshold(\text{same})}{2 * perturbationChannelLevel},$$

wherein II(probe, pert) is the interaction index of the probe and perturbation channels, probeThreshold(opposite) is the threshold of the probe channel measurement with the perturbation channel having the opposite polarity as the probe channel, probeThreshold(same) is the threshold of the probe channel measurement with the perturbation channel having an same polarity as the probe channel and perturbationChannelLevel is the sub-threshold level of the perturbation channel used in determining the probe threshold levels. In an embodiment, the probe channel thresholds and perturbation channel levels used in this formula are in linear current units.

The fitting system 306 or device 240 may then, at block 430, compare the magnitude of the computed interaction index (II) against the threshold to determine if the magnitude of the interaction index (II) falls below the threshold or not. If not, this indicates that the interaction between the probe and perturbation channels is significant. And, if so, the interaction is determined to be insignificant.

In addition to determining whether the interaction is significant or not, the fitting system 306 may also use this computed interaction index (II) in block 440 to determine whether the interaction is constructive or destructive. For example, in this example, if the interaction index (II) is positive (i.e., >0), the interaction may be determined to be constructive, and if the interaction index (II) is negative (i.e., <0) the interaction may be determined to be destructive at block 440.

As noted above, in blocks 450 and 460 the focus of the probe channel and/or perturbation channel may be increased or decreased by respectively adjusting the weights for the probe channel and/or perturbation channel. In a cochlear implant 100 using tripolar stimulation with an extracochlear electrode, the focus may be increased, for example, by fitting system 306 or device 240 increasing the magnitudes of the weights of one or both of the neighboring electrodes (e.g., electrodes 1 and/or 3) and decreasing the magnitude of the weight of the extra-cochlear electrode. For example, initially, the neighboring electrodes may be assigned a weight of −0.3 and the extra-cochlea electrode assigned a weight of −0.4. It should be noted that in this example, the weight of the center electrode is always set to +1.0 for tripolar stimulation and that the summed value of all the weights in a given channel is equal to 0.

In adjusting the focus, the fitting system 306 may increase the focus by, for example, increasing the magnitudes of the weights of one or both of the neighboring electrodes in steps of 0.05 and decreasing the magnitude of the weight of the extra-cochlea electrode in steps of 0.5 or 0.1 respectively. It should be noted these values are exemplary only. Similarly, the focus of the probe channel and/or perturbation channel may be decreased by decreasing the magnitudes of the weights of the neighboring electrodes and increasing the magnitude of the weight of the extra-cochlear electrode. It should be noted that this is but one example of how weights may be adjusted and other mechanisms may be used. For example, a scalar may be used to multiply or divide the weights in adjusting the weights. Or, for example, a mechanism may be used where the step size is adjusted such that a large step size is used initially and then reduced depending on certain conditions, such as if the interaction goes from constructive to destructive or vice versa.

As noted above, the method and systems of FIGS. 3-4 may be used for adjusting the weights for other types of complex channels besides tripolar channels, such as, for example, phased-array stimulation channels. The following provides an exemplary description of methods and systems for adjusting the weights for phased-array stimulation channels. In some embodiments, the default weights for phased array stimulation channels may be determined by computing the transimpedance matrix for the cochlear implant 100 and then inverting the transimpedance matrix to provide the weights for the stimulation channels.

Figure 7:
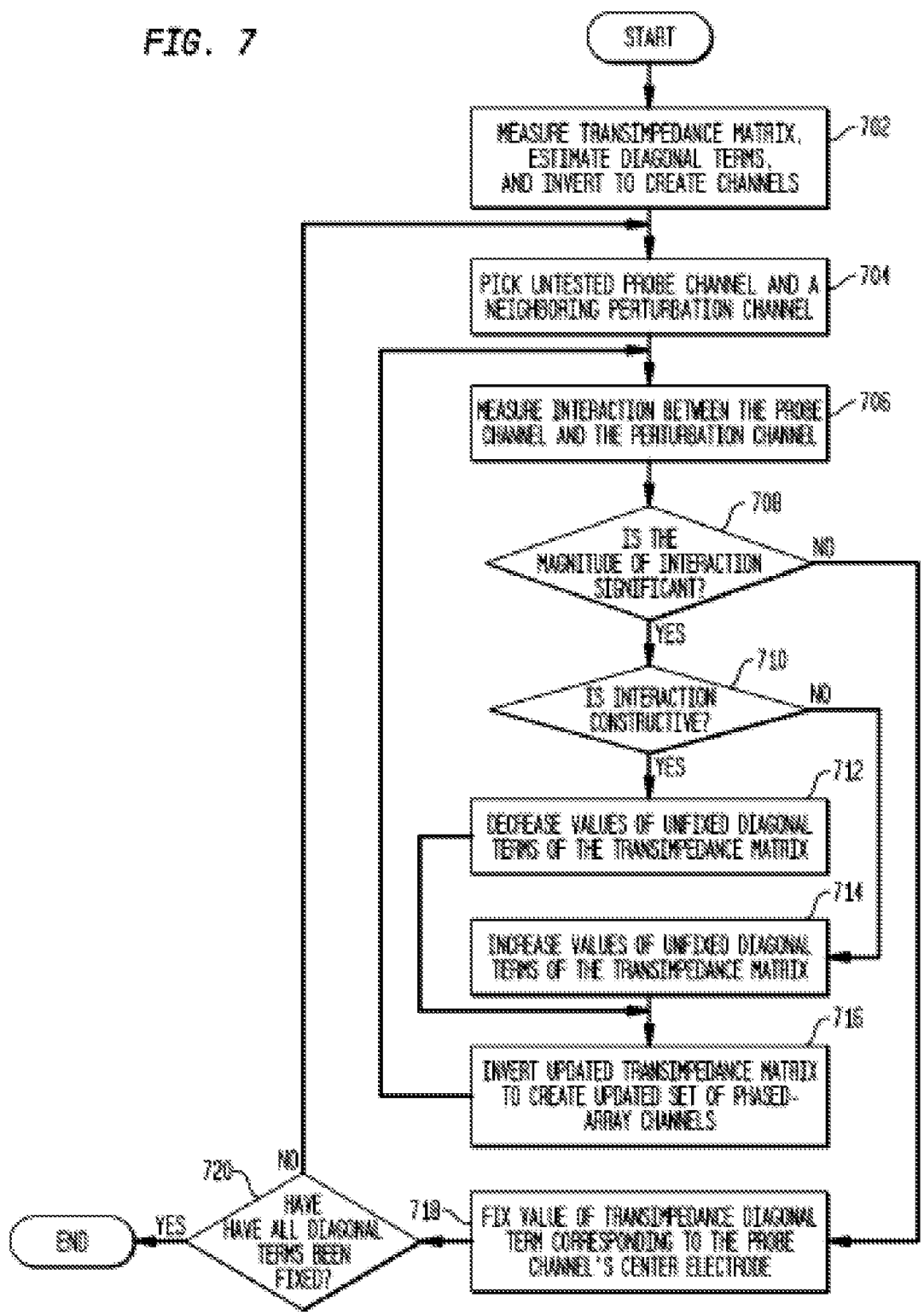
FIGS. 7 to 11 present flowcharts for exemplary algorithms.

FIG. 7 provides a flow chart for how the general method FIG. 4 may be used for adjusting the weights for phased-array stimulation channels, in accordance with an embodiment. FIG. 7 will be discussed in reference to the fitting arrangement system 300 discussed above. However, it should be noted that other systems may be used.

Initially, at block 702, an initial transimpedance matrix is obtained. This transimpedance matrix may be obtained according to any method that can have utilitarian value. An exemplary transimpedance matrix, $Z_m$, can comprises 22 columns and 22 rows. Each column and row corresponds to a particular electrode of an exemplary electrode array comprising 22 electrodes, where a row corresponds to the electrode on which stimulation is applied in measuring the transimpedance matrix. And, a column corresponds to the electrode on which the applied stimulation is measured in obtaining the transimpedance matrix. In some embodiments, all values, except the diagonal, of the transimpedance matrix may be empirically measured by stimulating each electrode with a known current, one at a time. Then, the resulting voltage at each non-stimulated electrode is measured. Because voltage observed on the stimulating electrode includes parts from the bulk resistance and tissue impedance, the diagonal of the transimpedance matrix is not determined in this manner. Rather, the values along the diagonal of the transimpedance matrix may be estimated by linear extrapolation of the values surrounding the diagonal values. Methods and systems for obtaining the transimpedance matrix and estimating the diagonal values 802. Although transimpedance matrix, $Z_m$, comprises 22 columns and 22 rows, it should be noted that this is exemplary only, and in other embodiments electrodes arrays comprising a different number of electrodes other than 22 may be used.

Once the transimpedance matrix is obtained with the estimated diagonal values, the fitting system 306 and/or the device 240 then inverts the transimpedance matrix to obtain an initial set of weights for the phased-array channels. Particularly each column of the inverted transimpedance matrix (also known as the transadmittance matrix) comprises a set of numerical weights (transadmittance values) defining the current contribution from each electrode for producing a non-zero intrascalar voltage at a single discrete stimulation region. As such, each such vector of weights defines a phased-array stimulation channel.

The fitting system 306 and/or device 240, at block 704, selects one of the stimulation channels as a probe channel and a neighboring channel as the perturbation channel. Interactions are then measured between the selected probe and perturbation channels at block 706. This may be accomplished in the same manner as discussed above with reference to block 420 of FIG. 4. Particularly, in an embodiment, the interaction may be measured by determining the threshold of the probe channel while simultaneously stimulating the perturbation channel at a fixed sub-threshold level.

The threshold of the probe channel may be measured twice, once with the perturbation channel having the same polarity as the probe, and once with the perturbation channel having the opposite polarity of the probe channel. The level of the perturbation channel is fixed for both threshold determinations. The above-discussed interaction index (II) may then be computed:

$$II(\text{probe, pert}) = \frac{probeThreshold(\text{opposite}) - probeThreshold(\text{same})}{2 * perturbationChannelLevel},$$

The fitting system 306 and/or device 240 may then determine, at block 708, whether the magnitude of the computed Interference Index (II) exceeds a threshold value. An exemplary threshold would be an II of 0.05, though other values other than 0.05 may be used depending on the accuracy of the interaction index measures. If threshold is exceeded, the fitting system may then determine, at block 710, whether the interactions are constructive or destructive. As noted above, the fitting system 306 may determine whether the interaction is constructive or destructive by checking whether the Interference Index (II) is positive (i.e., constructive interference) or negative (i.e., destructive interference).

If the interactions are significant and constructive, the fitting system 306 and/or device 240 may adjust the transimpedance matrix to increase the focus of the stimulation channels at block 712. This may be accomplished by decreasing all unfixed diagonal terms of the transimpedance matrix. The value of the diagonal term corresponding to a particular stimulation channel's electrode center, in embodiments, has the most significant impact on the focus of that stimulation channel. Accordingly, in other embodiments, the fitting system 306 and/or device 240 may only decrease the value of the diagonal term corresponding to the probe channel's electrode center, or a subset of the values surrounding this term, as opposed to decreasing the values of all unfixed terms.

If the interactions are significant and destructive, the fitting system 306 and/or device 240 may, at block 714, increase the values of the unfixed diagonal terms of the transimpedance matrix to decrease the focus of the stimulation channels. Or, for example, fitting system 306 and/or device 240 may only increase the value of the term corresponding to the probe channel's electrode center or a subset of the values surrounding this term. New channel weights are then computed from the updated transimpedance matrix, at block 716, and the iterative procedure continues by measuring interactions between probe and pert. channels using the new weights.

If, at block 708, the magnitude of the Interaction Index (II) is below the threshold, then, the iterative procedure is stopped for this particular probe channel and the fitting system 306 sets the final value of the diagonal term of the transimpedance matrix corresponding to the electrode center of the probe channel as fixed. The fitting system 306 and/or device 240 may set a diagonal term as fixed by simply storing an indication in a memory or other storage device that identifies that the particular diagonal term is fixed. The fitting system 306 and/or device 240, then, at block 720, determines whether all diagonal terms have been fixed. If not, the process returns to Step 704 where the optimization procedure is repeated for a different stimulation channel selected as the probe channel. This process then repeats until all channels have been tested as the probe channel, and all diagonal values have been fixed.

Referring back to blocks 712 and 714, the fitting system 306 and/or device 240 may adjust the diagonal term, such as the value corresponding to the probe channel's electrode center and/or the unfixed terms, in a variety of manners. For example, in an embodiment, a variable, referred to herein as a phased array compensation factor (PACF), may be used to determine a multiplication factor (MF). And, the diagonal term(s) may be adjusted by multiplying the diagonal term(s) by this multiplication factor (MF). In an embodiment, the relationship between the PACF and MF may be defined as follows:

PACF=1−(1/MF), or

MF=1/(1−PACF), where

0≤PACF≤1

In adjusting the diagonal terms, the fitting system 306 and/or device 240 may initially set the PACF to a particular value, such as, PACF=0.0 and then compute the corresponding MF (i.e., MF=1). Then, the fitting system 306 may multiply the diagonal terms (e.g., the unfixed terms, the diagonal term corresponding to the probe electrode center, etc.) by MF, and compute the II with the new diagonal terms. The PACF may then be increased by a particular step size (e.g., +0.2) with each subsequent iteration. That, in the next iteration PACF=0.2 and, thus MF=1.25. This step size (e.g., 0.2) may be used until the opposite condition occurs (i.e., the value of the Interaction Index (II) goes from negative to positive or vice versa). The step size may then be halved and its sign reversed (e.g., −0.1) and the process repeated. In other words, if increasing the PACF, an initial step size (e.g., +0.2), may be used until the Interaction Index (II) is positive (constructive), then the step size may be reduce (e.g., halved) and its sign reversed (i.e., reduced to −0.1) and used to reduce the value until the II becomes negative, and then reduced (e.g., halved) again (i.e. reduced to +0.05), and so on until the II value falls below the threshold. It should be noted that this is but one example of how the values of the diagonal terms may be adjusted and other methods can be used without departing from the invention as claimed.

For example, in an alternative embodiment, rather than adjusting one stimulation channel at a time and fixing the diagonal values at the end of each iteration, the system may not fix any terms until finalized and instead adjust all or some of the diagonal values on each iteration. It should, however, be understood that these are but some exemplary methods that may be used for adjusting the weights to minimize interactions and other methods may be used without departing from the invention.

At the end of the iterative process, when interactions between all possible probe channels and the corresponding perturbation channels (i.e., a channel neighboring the probe channel) are minimized, the fitting system 306 and/or device 240 may use the final values to generate the electrode weights for stimulation channels and then provide these weights to the cochlear implant 100. The cochlear implant 100 may then store and use these weights in the sound processing unit 126 and/or the stimulator unit 120. In another embodiment of the invention, the iterative optimization process for each probe/perturbation channel pair can be terminated early by estimating channel configurations at the point of insignificant interaction. For example, the estimation of channel configurations may be done by interpolating between iterations of optimization that respectively show constructive and destructive interactions. In another embodiment of the invention, the iterative optimization process for each probe/perturbation channel pair may never reach a point of insignificant interaction and the iterative procedure may be stopped at a minimum magnitude or estimated minimum magnitude of the interaction.

The methods and systems discussed above for measuring the channel interactions are merely one mechanism that may be employed for measuring the channel interactions. For example, in other embodiments, the fitting system may measure the channel interactions by simultaneously applying a stimulation signal on a probe and perturbation channel with the same polarities and comparing the determined probe threshold with the probe threshold determined during the set-up process, which was determined without the presence of any perturbation channel. This difference between the probe threshold in the presence of the perturbation channel and in the absence of the perturbation channel can be compared against a threshold. If the difference is greater than the threshold the focus of the probe channel may then be accordingly modified. Similarly, in another embodiment, stimulation signals may be applied on both the probe and perturbation channels, where the probe threshold is first determined with a perturbation channel of the same polarity and then with a perturbation channel of the opposite polarity. But, in this example, rather than setting the perturbation channel to a fixed subthreshold level, the probe and perturbation channels may be set and adjusted to the same levels, and the probe thresholds for each polarity determined in this manner. Then, the difference in probe thresholds for each polarity may be compared against a threshold value to determine whether or not the interactions between the channels are significant or not.

The above teachings can enable the achievement of fully optimized focused stimulation. However, it is noted that in at least some instances, fully optimized maps are time consuming to create. In accordance with at least some of the teachings detailed herein, there is now disclosed exemplary methods, and/or systems, and/or devices for creating a focused stimulation map slowly over time, such as at the convenience of the patient/recipient. In an exemplary embodiment, there are devices, systems, and/or methods that include removing the time-consuming burden from the clinician and/or at least limiting the amount of clinician time that would otherwise be the case in the absence of the teachings detailed herein. In at least some exemplary embodiments, some of the methods detailed herein can be used when switching from a different coding strategy or at initial activation of sound.

Switching from one map to another, such as a map that results in more focused stimulation relative to a previous map, can be difficult for some recipients. In at least some exemplary embodiments, the teachings detailed herein are implemented with respect to recipients that can have, as a statistical/demographic/fact determination, more difficulty adapting if the perceived change is abrupt, and where the more difficulty can be a statistically significant more difficulty. This can occur when transitioning between different stimulation modes, such as from monopolar stimulation to bipolar or tri-polar stimulation, and could result in rejection of a map that, if introduced differently, could provide the recipient of the prosthesis with improved hearing performance.

Additionally, in some exemplary scenarios, initial activation is a period of relatively higher change for the recipient relative to other periods. In some exemplary scenarios, initial activation is a period where adjustments are needed in or otherwise can be utilitarian if provided in a timely manner. Some exemplary embodiments of the teachings detailed herein can reduce wait time for mapping adjustments. Further, some exemplary embodiments can place control of the process, partially and/or fully in the recipient's hands, and/or take at least a portion of the control process out of the clinician's hands. Some exemplary embodiments can reduce the time spent by the clinician with a single recipient in clinic, relative to that which would otherwise be the case in the absence of the teachings detailed herein. Some exemplary embodiments of such can have utilitarian value with respect to allowing availability to use their skill in more complex cases rather than routine work that does not require a high level of expertise relative to that which would be the case in the absence of the utilization of the teachings detailed herein.

At least some exemplary embodiments include a fitting flow that gradually transitions from a monopolar (MP) to a focused map by providing the recipients of a hearing prosthesis with progressively more focused maps (although retro focused maps can be provided in some instances in between the provision of the more focused map(s)). At least some exemplary embodiments that utilize this workflow, the recipient can take as much time as needed to transition between maps at least some of them wear embodiments, this can have utilitarian value of minimizing at least some if not all undesirable perceptual changes resulting from changes in the stimulation mode.

At least some exemplary embodiments can be implemented utilizing home testing, such as that which results from the inclusion of at least some of the teachings detailed herein on an application on recipient's mobile device (e.g., smartphone, smartwatch, etc.) and/or on a computer (laptop, desktop, etc.) or personal computer, etc., to enable multiple map creations. In some embodiments, such can have utilitarian value with respect to avoiding overburdening the clinic with appointments for small changes and/or making the mapping convenient for the recipient. The application can, in at least some embodiments, allow recipient-driven measurements operating under restricted controls and a limited amount of change in one session. These restrictions can, in some embodiments, result in the providing of small, manageable changes that are made and/or a reduction (which includes avoidance/effective avoidance) of the likelihood of overstimulation and/or a reduced amount of such relative to that which would otherwise be the case in the absence of the teachings detailed herein.

An exemplary embodiment includes clinician input at various stages of the workflow, while in other exemplary embodiments there is no clinician input at various stages of the workflow. That said, in an alternative embodiment, the workflow is executed or otherwise conducted under the complete direction of a clinician.

In at least some exemplary embodiments, a primary parameter change in each transitional step and/or at least some of the transitional steps in a group of transitional steps is the degree of focusing. The step size for the change can be, in some embodiments, dictated by the type of focused stimulation mode. In some embodiments, default step sizes can be defined within the application itself and/or can be based on recommendations made by the clinician. In at least some exemplary scenarios of limitation, each time or at least some times that the level of focusing changes, the threshold (T) and comfortable (C) levels are assessed for audibility and equal loudness and/or adjustments are made to achieve such or at least achieve a result that is relatively close to such or otherwise effectively close to such. In at least some exemplary embodiments, the new map is evaluated using a variety of measures (i.e., speech perception, audiometric thresholds, spectral resolution testing, etc.—any measurement that will enable such evaluation can be utilized in at least some exemplary body) to determine benefit or otherwise to provide a measure of utilitarian value that can be compared to other scenarios or otherwise can be compared to other maps. In at least some exemplary embodiments, the process also includes the actions of evaluating hearing performance and/or the determination of whether further focusing is advisable or otherwise whether such might have utilitarian value and/or the determination of whether defocusing can be useful.

At least some exemplary embodiments, the methods that begin with implementation of the teachings detailed herein on a prosthesis that has been utilized to evoke hearing percepts for a meaningful period of time utilizing a stimulation regime at a first level of focusing vis-à-vis, for example, the tissue that is stimulated. In an exemplary embodiment, the temporal period where the prosthesis was used to stimulate a recipient at the first level is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or weeks, or months. In an exemplary embodiment, the first level of focusing corresponds to monopolar stimulation, where, in the case of a cochlear implant, current flows between an intracochlear active electrode and an extracochlear ground electrode. Because of the distance between these electrodes, the current spread is broad, and thus relatively less focused than other types of stimulation, in at least some embodiments. Stimulating in this way, in at least some embodiments, recruits large neural populations, thereby achieving higher loudness levels with lower current, all other things being equal, as compared to other types of stimulation. In some embodiments these broad neural activations limit spectral resolution due to interactions between neighboring channels.

Figure 5:
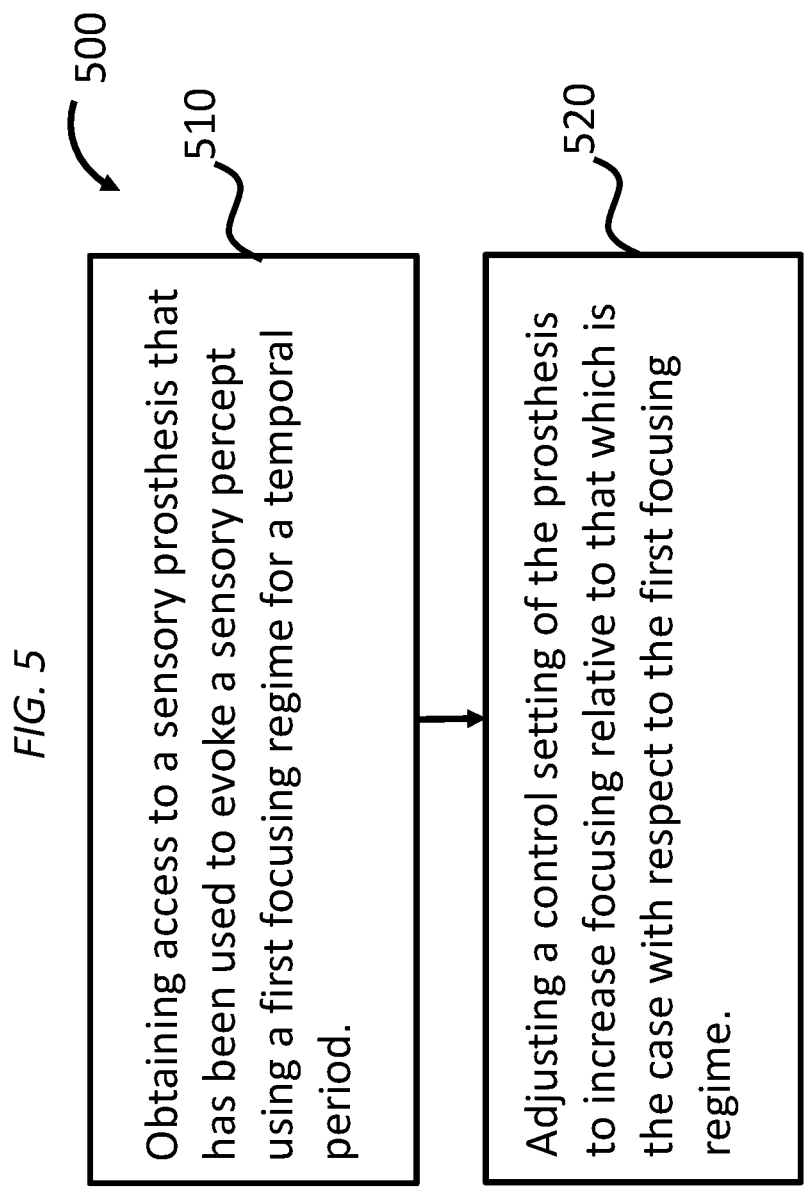

It is noted that while in some embodiments, the first level of focusing is monopolar stimulation, in other embodiments, it is bipolar or tripolar or focused multipolar. Note also that the first level of focusing is a name, and it is possible that a previous level of focusing existed. In any event, referring to FIG. 5, there is presented an exemplary algorithm exemplary method, method 500, that is a method of at least partially fitting a hearing prostheses device to a recipient, which method includes method action 510, which includes obtaining access to a sensory prosthesis that has been used to evoke a sensory percept using a first focusing regime for a temporal period. In an exemplary embodiment, the temporal period can be at least 0.1, 0.2, 0.3 0.4 0.5, 0.6, 0.7. 0.8, 0.9 or 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or weeks, or months, or years, or any values or range of values therebetween in 0.01 increments. These variations in the temporal periods are not arbitrary as the teachings detailed herein can be utilized across a wide range of human factors engineering recipients. Indeed, in an exemplary embodiment, the temporal period could be 5 or 10 years or more, such as, for example, where the recipient has utilized monopolar stimulation for years if not decades and now there is an effort to improve the life experience of the recipient utilizing more focused techniques. Conversely, in an exemplary embodiment, the temporal period could have been a few days or less, where the recipient is a new implant recipient and the recipient wants to move on with the habilitation and/or rehabilitation journey as quickly as possible, and the recipient is mentally and/or physically capable of doing so (eye of the tiger type people). To be clear, embodiments can include habilitation and/or rehabilitation regimes that utilize the innovative teachings detailed herein.

It is noted that in at least some exemplary embodiments, the aforementioned temporal periods and the temporal periods detailed herein correspond to at least a temporal period associated with acclimation of the given map or control settings. In at least some exemplary embodiments, the temporal periods are any of the temporal periods detailed herein. Again, this first focusing can be monopolar stimulation, or another stimulation regime, such as, for example, those detailed below.

Method 500 also includes method action 520, which includes adjusting a control setting of the prosthesis to increase focusing relative to that which is the case with respect to the first focusing regime. In an exemplary embodiment, the action of adjusting the control setting includes purposely adjusting the control setting to have focusing that is effectively less focused than a maximum focus possible. In an embodiment, this can have utilitarian value with respect to reducing the risk of (which includes avoiding) initial overstimulation which could result from applying focusing at a more focused level.

In an exemplary embodiment, the action of adjusting the control setting of the prosthesis includes replacing an existing map with a new map that results in the prostheses applying currents from the electrodes in a different manner relative to an old map, the old map being the map that was utilized to achieve the first focusing regime. In an exemplary embodiment, the old map could be a map for monopolar stimulation. In an exemplary embodiment, the old map could be a map for bipolar or tripolar stimulation, or a map for a less focused multipolar stimulation relative to a more focused multipolar stimulation achievable by the prosthesis.

In at least some embodiments, the focused stimulation modes that are used for certain control regimes can restrict current spread by varying degrees by, for example, simultaneously stimulating multiple intracochlear electrodes. This stimulation mode can use, for example, magnitude and/or polarities of the currents based on, for example, subject-specific impedance measurements (used to calculate the magnitude and/or polarities, for example), which magnitudes and/or polarities can create a desired voltage at a central electrode while zeroing out the voltages on one or more or all other electrodes. This can have utilitarian value by stimulating in a more spatially-selective manner than monopolar stimulation. In some embodiments, it is noted that the more spatially selective neural activation can be coupled with higher current levels to reach threshold and comfortable listening levels relative to that which might otherwise be the case in the absence of the focusing/that which would result from the monopolar stimulation, all other things being equal.

Figure 6:
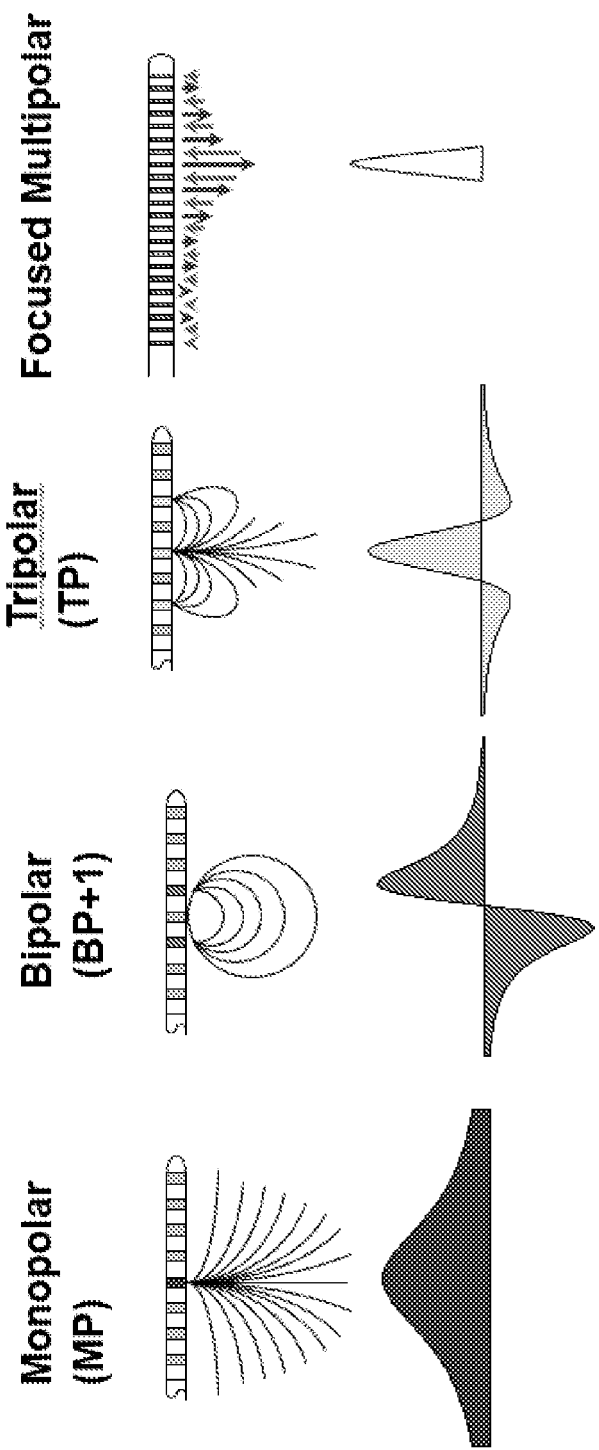
FIG. 6 presents conceptual concepts of stimulation.

An exemplary embodiment includes executing method action 510 and method action 520 repeatedly so that there is a smooth(er) transition from monopolar stimulation to focused multipolar stimulation (FMP), as distinguished from bipolar and tripolar stimulation. FIG. 6 presents an exemplary graphic conceptually representing the various types of stimulation.

Some embodiments include transitioning from monopolar to other focused stimulation modes including but not limited to bipolar and tripolar. In bipolar stimulation, current is sourced from one intracochlear electrodes and returned on a neighboring intracochlear electrode. In tripolar (TP) stimulation, current is sourced from an intracochlear electrode and returned to the two flanking intracochlear electrodes. FIG. 6 illustrates the current paths and voltage patterns resulting from each stimulation mode.

Accordingly, in an exemplary embodiment, the first focusing regime of method action 510 is monopolar stimulation, and in method action 520 the action of adjusting the control setting includes implementing a second focusing regime that is pluralpolar stimulation (bipolar, tripolar, partial tripolar, or focused multipolar with less focusing than that which could be achieved). Corollary to this is that in an exemplary embodiment, the first focusing regime is one of monopolar stimulation, bipolar stimulation or tripolar stimulation and the action of adjusting the control setting includes implementing a second focusing regime that is a focused multipolar regime.

Again, in some embodiments, the path of progression can be initially starting with monopolar stimulation, and then moving to bipolar, and then moving to tripolar, and then moving to a focused multipolar stimulation at a first focusing level, and then moving to a second focusing level and then to a third focusing level and then to a fourth focusing level and then to a fifth focusing level and so on, each level being more focused than the previous level, although one other embodiments, there could be levels which entail less focusing than the previous level for various reasons, such as in a scenario where the level of focusing was premature.

An exemplary method can include the action of opening a parent map, which is the last accepted map (e.g., the first focusing regime of method action 510). It is noted that a given map can include focusing for each specific channel. This will be described in greater detail below. It is noted that the last level of focusing can be determined for each channel in the map in at least some exemplary embodiments. The method then further proceeds to the determination of a new level of focusing. In an exemplary embodiment, the degree of focusing that can be utilitarian to achieve maximization of performance may vary across channels. For example, channels in the apical region may need to be more focused than in those in the basal region to achieve a given outcome, all other things being equal. In this step, the level of focusing can be increased by a small amount for all channels (except if compliance limits or performance outcomes result in a focusing limit for all or a subset of channels). This increase in level of focusing can correspond to the adjustment of the control settings of method action 520 detailed above.

In an exemplary embodiment where there is transitioning from monopolar stimulation to, for example, tripolar stimulation and/or other focused stimulation modes, where a current i is delivered to an active intracochlear electrode and the return current i/2 is delivered to each of the flanking electrodes, such can be considered, for example, maximum focusing in some exemplary embodiments. This could be the result of repeating method 500 a number of times and/or repeating any of the other methods detailed herein a number of times. An exemplary embodiment of the execution of method action 520 can include first implementing a stimulation regime that results in a partial tripolar configuration, where a fraction of the return current, $(\alpha \cdot i)/2$, is delivered to each of the flanking intracochlear electrodes, and the remainder of the return current, $(1-\alpha) \cdot i$, is delivered to a grounding extracochlear return electrode. The amount of focusing can be controlled by varying $\alpha$ form 0 (equivalent to MP) to 1 (standard TP). Accordingly, in an exemplary embodiment, there is an exemplary method, method 800, which includes method action 810, which includes executing method 500, where $\alpha$=0.X, where X can be, for example, 9 (i.e., alpha equals 0.9, creating a channel close to standard tripolar). That is, the adjustment of the control setting results in 90% of the return current flowing to the two flanking intracochlear electrodes (45% to each one), and 10% of the return current flowing back to the grounding extra cochlear electrode. Method 800 further includes method 820, which includes further adjusting the control setting of the prosthesis to increase focusing relative to that which is the case with respect to the focusing prior to the increase, wherein $\alpha=\alpha-Y(n)$, where Y(n) can be, for example, 0.1 for n=1 (and if alpha was 0.9, it is now 0.8). This can go on for a number of times for various values of Y(n), which can be the same for each n or can be different. Thus, in an exemplary embodiment Y(1) can be 0.1, Y(2) can be 0.3, Y(3) can be 0.1, and Y(4) can be 0.4, and thus after four iterations (n=4), there would be full focusing. In an exemplary embodiment, X can be 999, 950, 99, 98, 97, 96, 95, 94, 93, 92, 91, 90, 85, 80, 75, 70, 65, 60, 55, 50, 45, 40, 35, 30, 25, 20, 15, 14, 13, 12, 11, 10, 9, 8, 7, 6, 5, 4, 3, 2, or 1, or 0.1, or 0.001, or any value or range of values therebetween in integer increments (e.g., 944, 36, 997 to 3, etc.) or any value or range of values therebetween in 0.001 increments. Further, Y can be 0.999, 0.950, 0.99, 0.98, 0.97, 0.96, 0.95, 0.94, 0.93, 0.92, 0.91, 0.90, 0.85, 0.80, 0.75, 0.70, 0.65, 0.60, 0.55, 0.50, 0.45, 0.40, 0.35, 0.30, 0.25, 0.20, 0.15, 0.14, 0.13, 0.12, 0.11, 0.10, 0.09, 0.08, 0.07, 0.06, 0.05, 0.04, 0.03, 0.02, or 0.01, or 0.001, or any value or range of values therebetween in 0.001 increments, and again, Y need not be the same for each iteration, although in other embodiments, it can be the same.

It is noted that n can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 120, 130, 140, 150, 160, 170, 180, 190, 200, 250, 300, 350, 400, or 500 or more, or any value or range of values therebetween in integer increments.

It is further noted that in some exemplary embodiments, the values of Y and X can be different for each channel. In this regard, exemplary embodiments include repeating method actions 810 and/or 820 for each channel or for groups of channels separately with different values.

The above is contrasted to a traditional approach where, for example, X would be immediately set to zero at method action 810 (actually, there would not be any method action 810, as that requires executing method 500, which requires setting the control settings to have focusing that is less focus than the maximum focused possible.

It is also noted that embodiments include transitioning from a monopolar stimulation to a focused multipolar stimulation regime. In an exemplary embodiment, there are method actions that include the creations of new channels with new/different levels of focusing.

Figure 8:
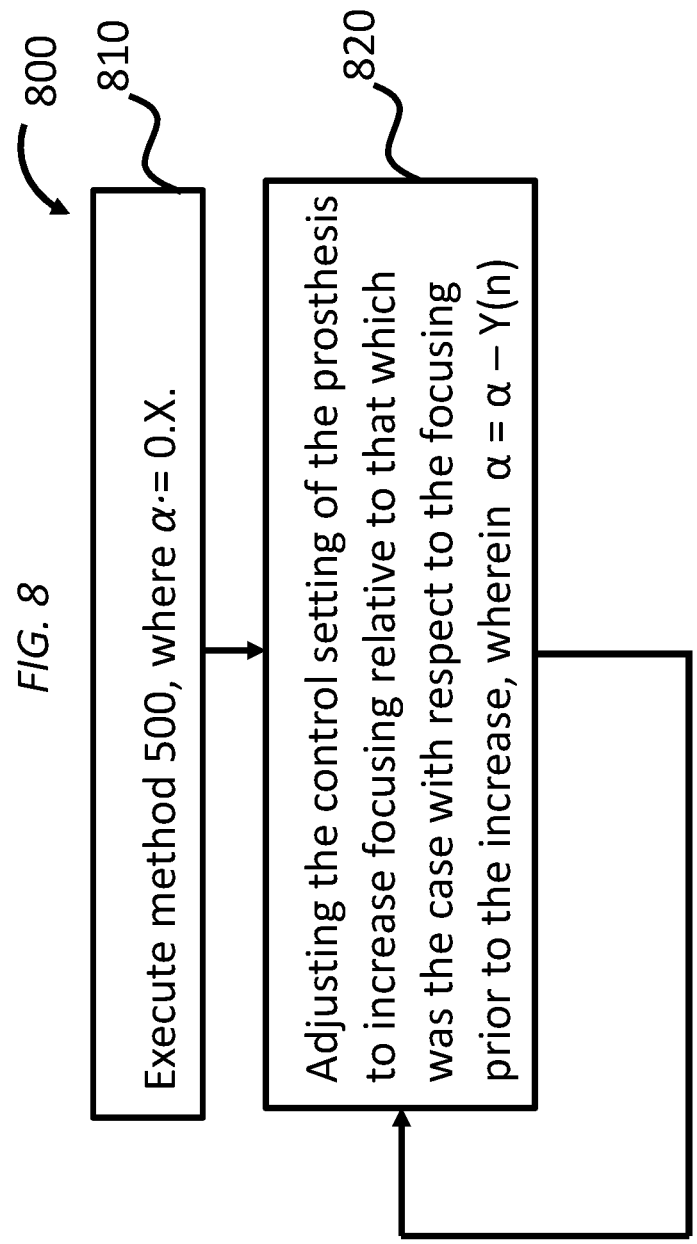
Figure 9:
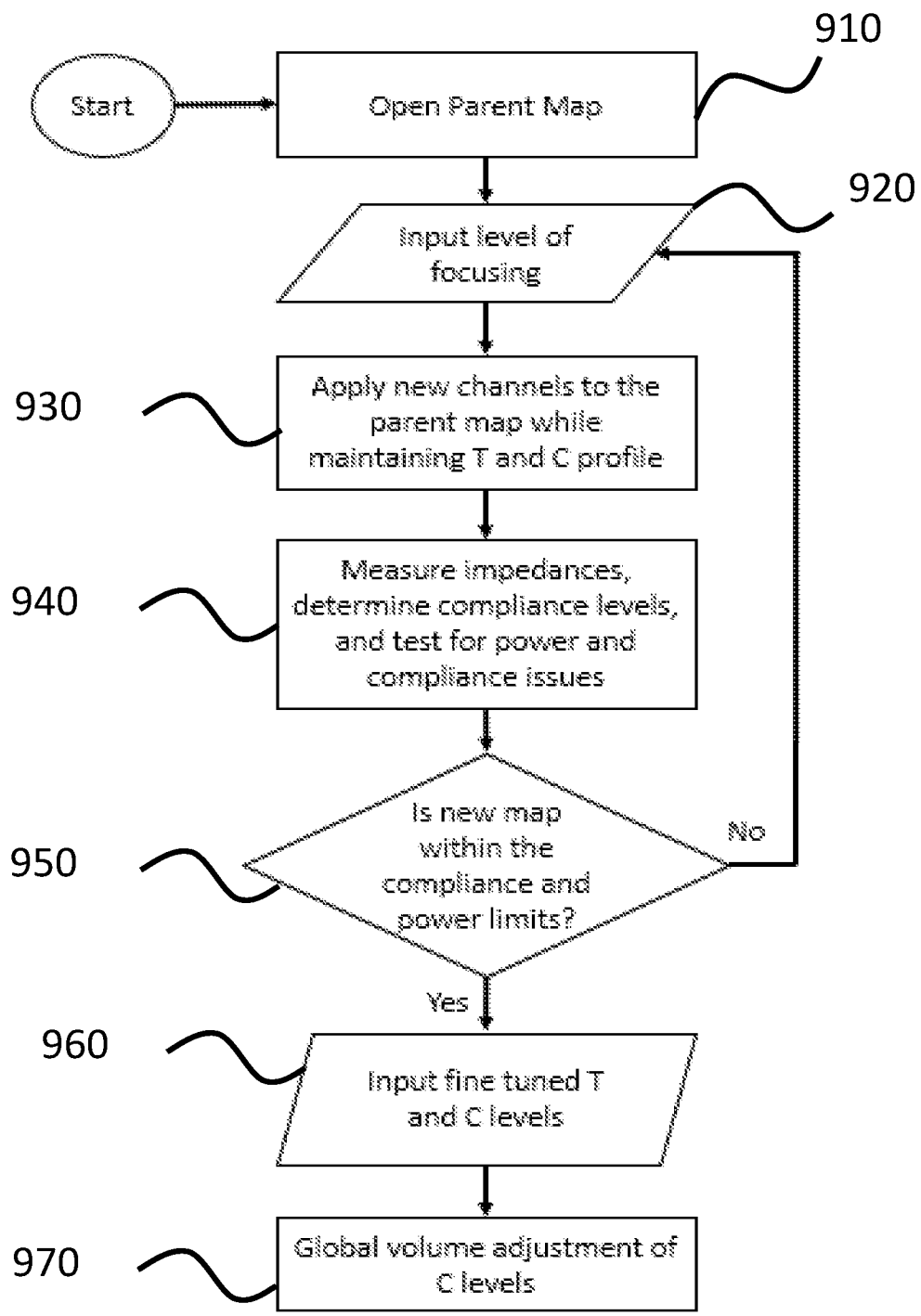

In view of the above, with reference to FIGS. 8 and 9 as a frame of reference, it can be seen that in an exemplary embodiment, there is a method that includes, after executing method 500, obtaining second access to the sensory prosthesis after the sensory prosthesis has been used to evoke sensory percepts using the adjusted control setting for a second temporal period (e.g., a week or a few days or longer or shorter, or a period of acclimation, etc.) and adjusting a control setting of the prosthesis a second time to increase focusing relative to that which is the case with respect to the focusing of the adjusted control settings for the second temporal period. Again, in at least some iterations of the methods according to the teachings detailed herein, the action of adjusting the control setting a second time includes purposely adjusting the control setting to have focusing that is effectively less focused than a maximum focus possible.

Consistent with the introduction of the "n" variable, and an exemplary embodiment, again after executing method 500, there is a first action of obtaining nth access to the sensory prosthesis after the sensory prosthesis has been used to evoke sensory percepts using the adjusted control setting for an nth temporal period, which can be any of the temporal periods detailed herein. There is also a first adjusting of a control setting of the prosthesis an nth time to increase focusing relative to that which is the case with respect to the focusing of the adjusted control settings for the nth temporal period. Also, the action of adjusting the control setting the nth time includes purposely adjusting the control setting to have focusing that is effectively less focused than a maximum focus possible. In an exemplary embodiment, there is repetition of the first action and the first adjusting for n equals at least any of the values detailed herein (e.g., 5, 10, 15, 20, 25, 30, 40, 50, 60, 70, 500, 600, 700, 800, 1000, 1500, etc. —noted that some exemplary embodiments include potentially a lifetime of improved focusing, if not a generation of improved focusing).

The idea is that in at least some exemplary embodiments, there can be utilitarian value with respect to gradually and incrementally increasing the level of focusing without upsetting the recipient or otherwise overwhelming the recipient. By rough analogy, this can be akin to a person gradually turning on lights after sleeping in darkness for a period of time so that his or her eyes can become accustomed to the light.

Consistent with the teachings above, channels could be created using a new transimpedance measurement for each new map. In an exemplary embodiment, prior to executing method action 520, there is the action of calculating or otherwise identifying weights for each channel or for at least one or more than one channel, which can be done, for example, by utilizing a transimpedance matrix as described above. In an exemplary embodiment, the desired level of focusing for a given channel can be used to scale the diagonal terms of the transimpedance matrix, which can then be inverted to create the individual channels. In another embodiment, by way of example only and not by way of limitation, after scaling the diagonal terms of the transimpedance matrix, only the portion of the matrix corresponding to the electrodes that will be stimulated for a given channel is pseudo-inverted. The row of this pseudo-inverted matrix corresponding to the desired channel is then selected to obtain the desired focusing weights for this channel. This process is repeated for each channel. In some embodiments, channels could be created using a previous transimpedance measurement. That is, in some embodiments, the same transimpedance measurements can be used for some or all of the values of n. Further, generic channels generated without subject-specific transimpedance information could also be used. In an exemplary embodiment, these channels could be created in a number of different ways, including using models of current flow in the cochlea, average transimpedance matrices or average channels derived from a large number of listeners, or by applying a pre-determined cancelation pattern to non-central electrodes. Any method or basis for developing focusing data that can enable the teachings detailed herein can be used in some embodiments.

Figure 10:
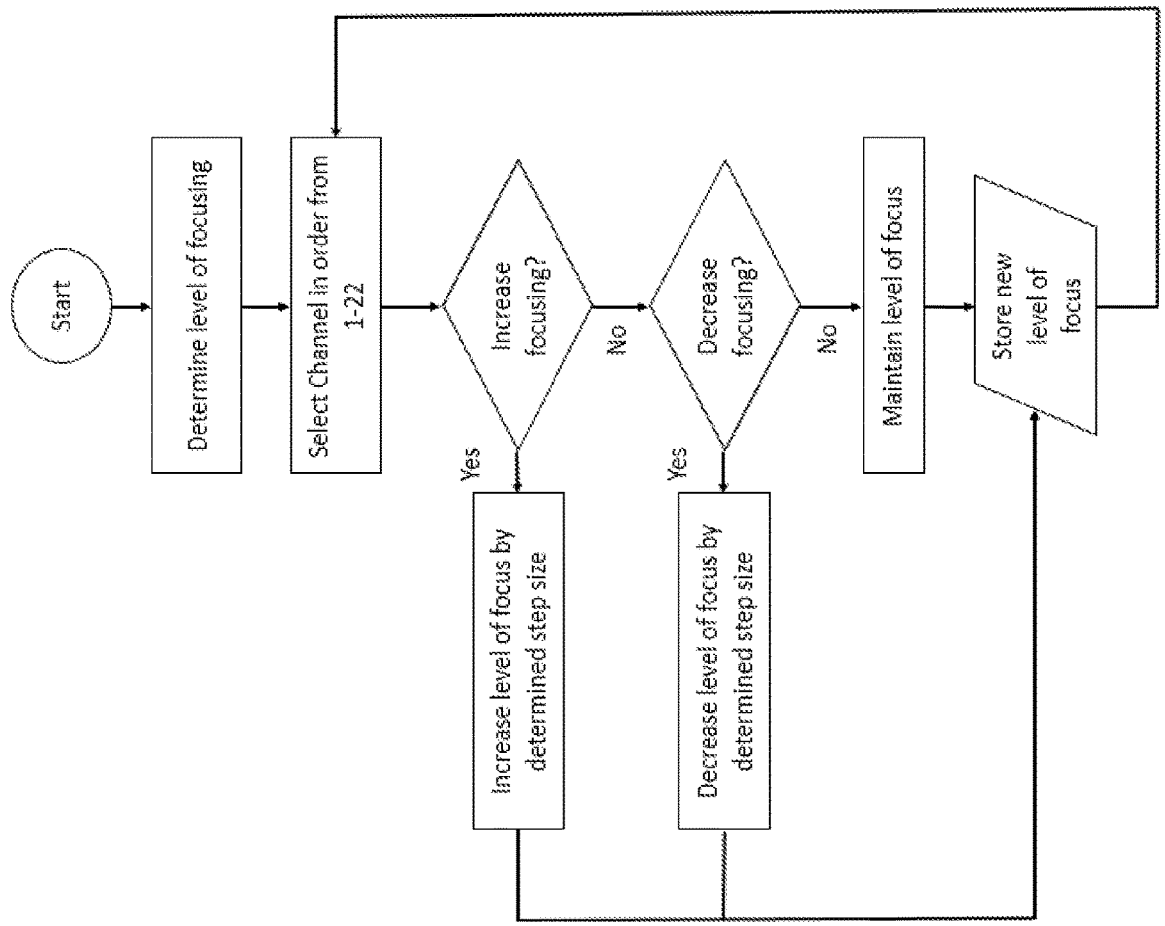

FIG. 9 presents an exemplary algorithm for an exemplary method, method 900 which includes method action 910, which is detailed above, which entails opening the parent map of the prostheses, which can be done for the utilitarian purpose of determining the current focusing settings if any. Method 900 also includes method action 920, which includes inputting into a device configured to execute at least some of the teachings detailed herein, such as the device 240 detailed above, the level of focusing that is desired with respect to the progressive map that is to be implemented. Method 920 can be preceded by a subroutine represented by FIG. 10, which is a subroutine for determining a level of focusing. Method 900 further includes method 930, which includes applying new channels to the parent map/replacing the parent map, while maintaining/keeping threshold (T) and comfortable (C) profile the same as the parent map prior to the application/replacement. This can be executed by any device, system, and/or method that can enable such, such as by making adjustments to specific portions of the existing map/tweaking the existing map for replacing the map with a new map, etc. Further, in an exemplary embodiment, the prosthesis can be operated in a master/slave mode without necessarily reprogramming the map or otherwise replacing the map that is stored in the prostheses (until the new map is decided upon). In this regard, a temporary new map can be developed or otherwise utilized which can be utilized as a basis to temporarily control the prosthesis until a determination is made as to the efficacy of the new focusing regime.

Method 900 further includes method action 940, which includes measuring impedance and/or determining compliance levels and/or testing for power and/or other compliance issues. That said, method action 940 can include any other measurements or determining action where the results thereof can of utilitarian value with respect to evaluating the adjustments that are to be made to the prostheses to increase focusing. Thus, this leads to method action 950, which includes determining whether the new map/adjusted map is within the compliance power limits or self-imposed power limits or any other limits/variables. If power or out-of-compliance issues are found for one or more or all of the channels, changes can be made to focusing levels to better meet power and compliance, and then the routine returns to method action 920, and if no issues are found, the routine continues to method action 960. Method action 960 includes fine tuning T and C levels. Here, because the increased level of focusing causes the stimulation to be concentrated, in at least some instances, the resulting current levels in a given channel will result in different loudness perceptions relative to that which would be the case without the increased focusing. That is, in some embodiments, as the maps become more focused relative to prior maps, T and C levels become less uniform across channels. Additionally, as focusing increases, it can become utilitarian, if not necessary to adjust the levels, such as increase the levels, so as to provide sufficient loudness/maintain a standard of loudness to which the recipient has acclimated himself or herself. Soft and loud levels can be balanced across the array to achieve or otherwise approach equal volume and comfortable listening levels.

In an exemplary embodiment, stimuli are presented from the test interface (e.g., application on recipient's mobile device or a clinician's PC or any other device) directly to the sound processor of the hearing prosthesis.

Figure 11:
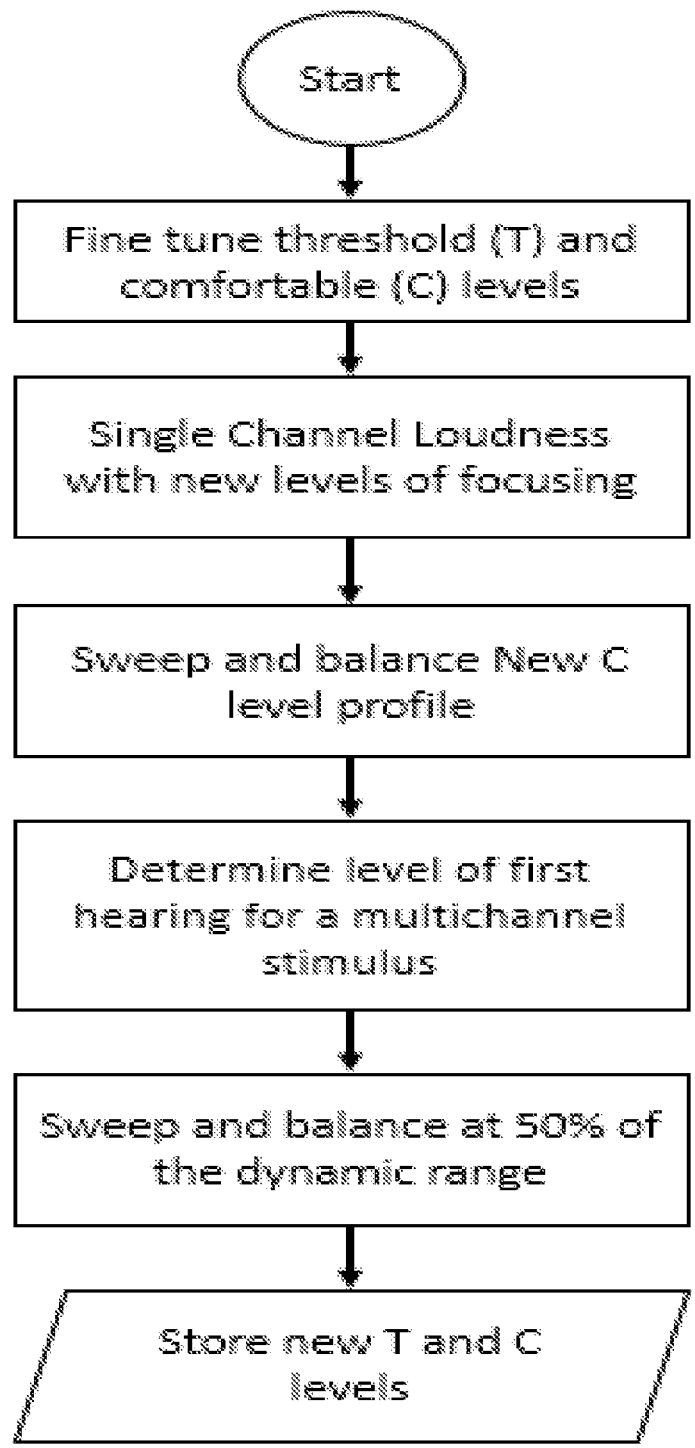

FIG. 11 presents an exemplary algorithm for an exemplary method of executing or otherwise obtaining data to implement method action 960. In an exemplary embodiment, single channel loudness testing/evaluation/adjustment is executed. For example, after the new levels of focusing are applied to the pertinent channels, C level values are retained from the parent map, and can be applied in a proto-new map for the moment, and, if acceptable, can be used, but in some embodiments, may be perceived at a different loudness by the recipient. The channels from the new map might require a balancing procedure to ensure appropriate/utilitarian/acceptable loudness perception and/or to obtain a new C level profile.

In an exemplary embodiment, a test interface is used to present stimuli during a 3-interval balancing task (A/B/A).

This can be performed through the device 240 detailed above. In an exemplary embodiment, the reference stimuli is the C level of the parent map for a given channel (A). The C level for the new map channel (B) will be adjusted to match A, by any method or device or system that can enable such, such as by a beep test, etc. The recipient increases increase or decrease "B" to match the loudness in "A". The balanced levels are then used to create the new C level profile.

In an exemplary embodiment, the recipient can place control inputs into device 240 to increase or decrease "B" so as to achieve sound generation of the like for comparison purposes to "A." In an exemplary embodiment, device 240 can be configured to provide an automated or semiautomated routine to provide stimulation to the recipients of the recipient can make a determination as to what should correspond to the new C levels. Any arrangement that can have utilitarian value and otherwise can enable the fine tuning of T and/or C levels can be lies in at least some exemplary embodiments.

Having established C level profiles for one or more or all of the channels at issue, typically individually, there is utilitarian value with respect to attempting to harmonize or otherwise achieve a C level profile as a whole the results in an equal loudness or at least something approaching equal loudness across the array. In this regard, there is further a method action of adjusting individual channel C levels to ensure or otherwise approach equal volume for each C level. This could be done in small groups (for example, groups of 5) of consecutive channels. Channels 1, 2, 3, 4, and 5 can be presented to the recipient and adjustments can be made, then channels 2, 3, 4, 5, and 6 can be presented to the recipient and adjustments can be made, and so on. Alternatively, 1-5 and then 6-10 and so on can be presented. C levels can be swept in both directions in at least some exemplary embodiments during this method action.

In an exemplary embodiment, the recipient can indicate if a channel is louder or softer than the rest of the group, such as by providing input into device 240 via the touch screen, or by simply speaking in a manner that the sound capture device of the prostheses or of the device 240 captures the sound, and a voice recognition system of the overall system can evaluate the input from the recipient. The test interface or other system that is utilized to implement the teachings detailed herein can make an adjustment to the protomap and then re-test until all channels are perceived as having the same volume for a given level of ambient sound/input sound. An optional second stage sweep of multi-channel C levels could also be completed to increase the likelihood that the overall loudness is comfortable.

After executing the above actions, the C levels for the given channels are then accepted/set for the new map, and the method then proceeds to develop/set new T levels. In this regard, there is then the action of determining the level of first hearing with respect to multichannel stimulus. In this regard, it is noted that perception of soft sounds will likely be in need of adjustment after the new focusing map is developed. The recipient can measure individual channel T levels (such as, for example, via the counting method) to obtain a new T level profile. The test interface can be configured to prepare the multichannel stimuli for the recipient. It can be configured to automatically create a 5-current level, for example (or any other value that can have utilitarian value) dynamic range T and C profile by reducing C levels to +5 current levels (or any other value) above the new T level profile. The test interface can then reduce the +5 CL T and C profile until inaudible (approximately 15-20 CL below the newly measured T level profile). The test interface can be configured to turn on live speech via the sound processor microphone or present pre-recorded speech and/or signals with similar spectral and/or similar temporal information to speech via the test interface and/or via direct input into the sound processor of the prosthesis and increase the +5 CL T and C profile until the recipient indicates first hearing. The test interface will retain the first hearing T profile and return the C level profile to the levels determined in the previous step. Each multichannel stimulus could be comprised of a small group of neighboring electrodes or all electrodes in the array.

FIG. 12A presents a schematic conceptually representing a three-space data block for a given channel, channel 15, for example. Block "A" is the split between the ground and the intracochlear electrodes, a, block "B" is the comfort level expressed in current level terms, and block "C" is the threshold level, again expressed in current level terms. At the beginning, the parent map has a value of alpha equal to 0.50, a comfort level of 60 CL, and a threshold level of 30 CL. The focusing is adjusted to alpha equal 0.75, and the comfort level testing indicates a comfort level of 63 CL, with an undetermined threshold level at the moment. Threshold level testing indicates a threshold level of 34 CL for the alpha equal to 0.75, this being determined via the counting method or the like. Then, utilizing the aforementioned exemplary+SCL method, the comfort level and the threshold level are both adjusted downwards to 30 CL and 17 CL respectively. The comfort level and threshold levels are then gradually increased to where a determination is made that the real threshold level is 32 CL. The data block is then finalized utilizing the new C level of 63 CL and the finalized T level of 32 CL, for alpha=0.75. Thus, this can be considered a finalized data block (or almost finalized data block—more on this below) for channel 15 for the new focusing regime.

Figure 12B:
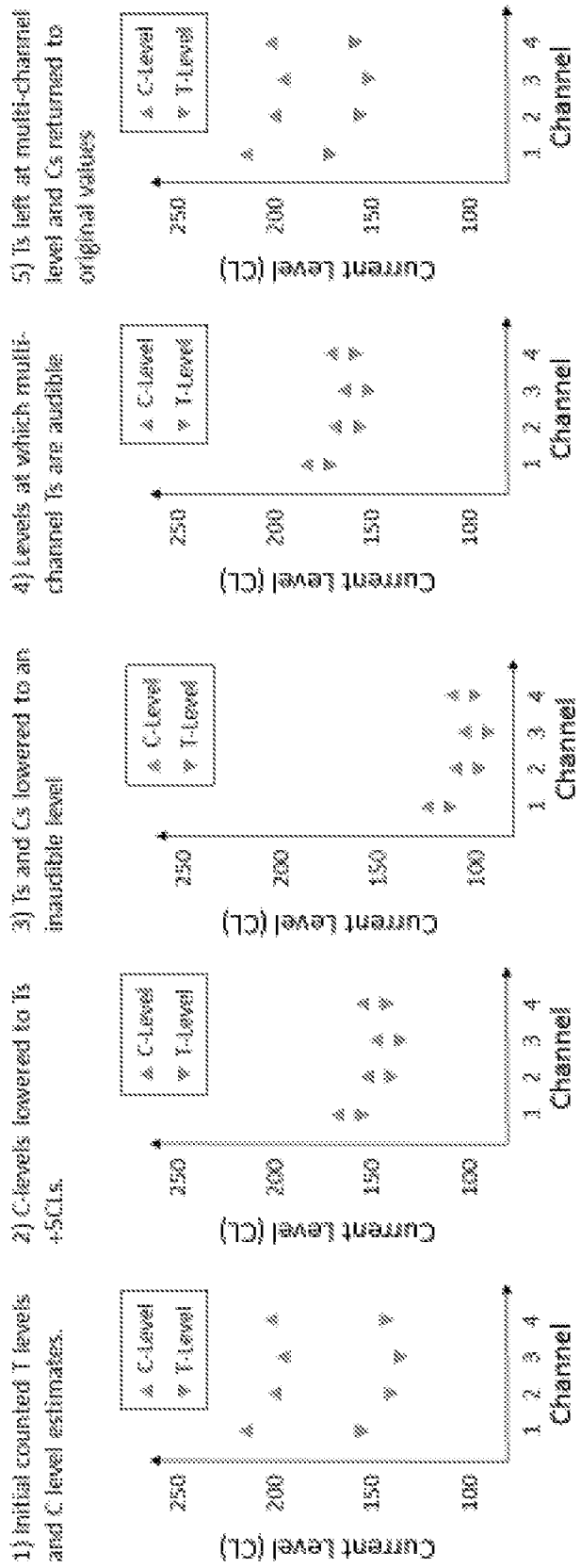
FIG. 12B presents an exemplary schematic conceptually representing another exemplary method.

FIG. 12B presents a schematic conceptually representing an alternate exemplary embodiment, where a group of 4 neighboring channels are presented, with T and C levels indicated by the downward and upward pointing triangles, respectively. These levels have been determined after adjusting the focusing level for these channels as previously described. In step 2, to obtain a multi-channel T level, the C levels are first lowered to a level equal to that of the T levels+5 CLs (again, the amount can be different in some embodiments). Then, in step 3, both the T and C profile are lowered together such that the resulting stimulus is inaudible (below the counted T levels in step 1). In step 4, these levels are raised together until the listener reports first hearing the stimulus. Then, in step 5, the C levels are returned to their original values while the Ts are kept at the level that resulted in a level of first multi-channel hearing. This process can be performed by grouping any number of adjacent channels, from 2 to as many as the device includes (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 80, 90, 100 or more or any value or range of values therebetween in 1 increments). Thus, this can be considered a finalized data block (or almost finalized data block—more on this below) for channel 15 for the new focusing regime. This process would be repeated for other blocks until all channels are adjusted in this manner.

That said, in an exemplary embodiment, a sweep and balance routine is executed at, for example, 50% of the dynamic range, to further fine-tune all almost finalized data blocks) across the spectrum. In an exemplary embodiment, 50% levels are swept in both directions. The recipient would indicate if any channels are louder or softer than the rest of the group. The test interface can be configured to automatically make any utilitarian adjustments to the C and T levels, etc., and can automatically initiate retesting until all channels are about the same volume.

Also, it is noted that in an exemplary embodiment of method 900, there is method action 970, which includes the global volume adjustment of C level. This can include globally adjust C levels to comfortable levels, where the stimulus could be live speech presented via the sound processor microphone or a stimulus presented from the test interface directly to the processor. This step could be optional in some embodiments.

After executing method action 970, if executed, the data blocks for the given channels are then finalized, and are used in the new map for the new focusing regime. The recipient then uses the new focusing regime as part of his or her everyday life.

In some embodiments, there is a bailout option, where the new map can be thrown over the side, or otherwise sidelined, if the recipient does not like such. This can entail reverting back to the prior map and/or making further adjustments to the new map. By way of example only and not by way of limitation, there can be a feature where the recipient can input data indicative of his or her displeasure with the new map. The system could automatically divide the focusing in half for example, or reduce it by one third, or something or other, to see whether that is less "traumatic" or otherwise disruptive to the recipient. An automatic iterative process could be applied where the system continuously reduces the focusing until the recipient finds such acceptable. It is noted that the T and C levels could remain constant in some embodiments, while in other embodiments, the T and C levels can be extrapolated in a linear and/or a nonlinear manner, between that which was developed for the new map, and that which was the case for the old map. Any form of statistical analysis that can have utilitarian value that can try to "salvage" the new map or otherwise salvage at least some of the changes so that the efforts can result in something that can be utilized in at least some exemplary embodiments.

Figure 13:
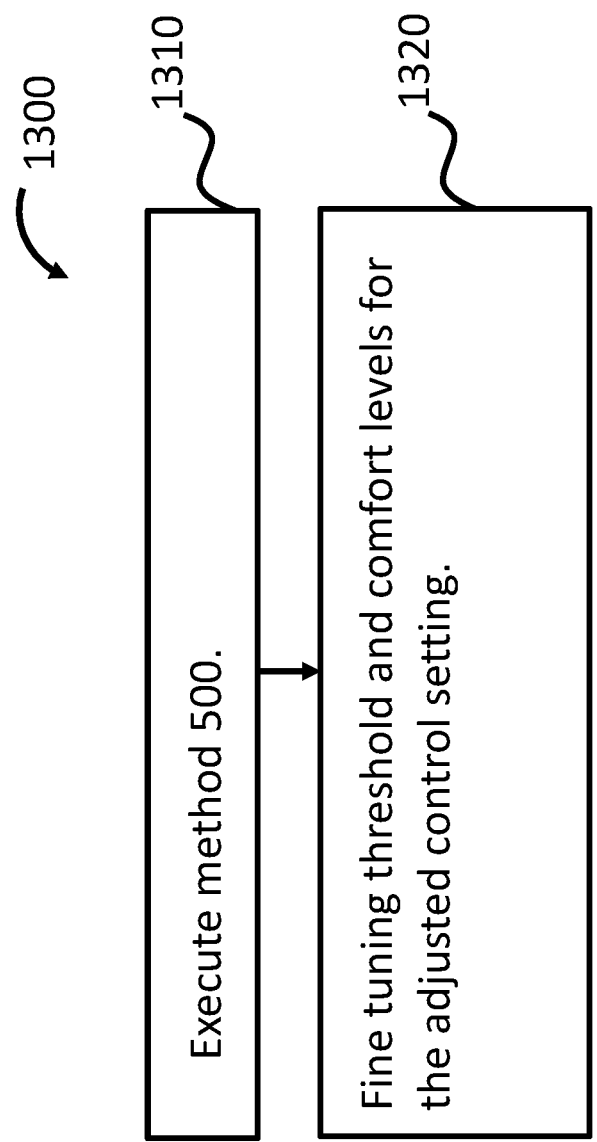
FIGS. 13-16 present flowcharts for exemplary algorithms.

In view of the above, it can be seen that in at least some exemplary embodiments, there is a method according that which can be represented by the algorithm of FIG. 13, which represents method 1300, which includes method action 1310, which includes executing method 500 method 1300 further includes method action 1320, which includes fine tuning threshold and comfort levels for the adjusted control setting that was adjusted in method action 520. Method action 1320 can include any of the actions detailed herein with respect to the adjustment of the T and/or C levels.

Consistent with the themes above associated with some exemplary embodiments, the actions of fine tuning threshold and/or comfort levels can be executed by the recipient of the prosthesis without at least active involvement of a sensory professional, such as an audiologist or otherwise a hearing prosthesis expert. That said, passive involvement can be implemented, such as, for example, where the healthcare professional evaluates the changes at a later date or otherwise is asked to approve a change before it is ultimately accepted and/or used by the recipient. By way of example only and not by way of limitation, a change might be relatively drastic in a manner where there can be utilitarian value with respect to the audiologist giving the change a sanity check or the like before it is implemented.

The above said, in some embodiments, there is absolutely no involvement of the sensory professional or the like with respect to the actions of fine tuning, etc. Conversely, in some embodiments, any one or more all of the actions disclosed herein are executed with the involvement of an audiologist or otherwise a healthcare professional or a sensory professional, etc.

In view of the above, there is a system for at least partially fitting a prosthesis to a recipient, comprising a device configured to control stimulation to evoke a sensory percept using the prosthesis. In this regard, this can be any sound processor of a hearing prosthesis or a light processor of a vision prostheses, etc. Also, these can be less sophisticated processors which simply contain programming perform simple tasks that ultimately result in the evocation of a sensory percept. Also, this can be computer chips or the like, or even general circuitry.

The system also includes a device configured to enable the recipient to make adjustments to focusing of the prosthesis with respect to tissue stimulation. By way of example only and not by way of limitation, this can correspond to device 240 detailed above, or any other computational device that can enable this functionality, such as a program on a computer, or even a non-smart phone that is in communication with a remote server or the like, etc.

Thus, it can be seen that the aforementioned system can correspond to system 210 of FIG. 2A detailed above, as modified with programming to correspond to this embodiment.

In an exemplary embodiment, device 240 can have an application thereon that corresponds to the above-noted test interface or the like or otherwise has the functionality of such, where the recipient can interact via touchscreen or via voice controls, etc., to input information and/or receive information there from to implement the teachings detailed herein. In an exemplary embodiment, device 240 can be programmed or otherwise configured to have the functionality that will enable one or more all of the method actions detailed herein. In an exemplary embodiment, device 240 could prompt the recipient after a certain period of time utilizing a given map to ask recipient if he or she would like to move up in a map or otherwise improve the focusing of the prostheses. Note also that in an exemplary embodiment, device 240 could prompt the recipient after a certain period of time utilizing a given map to obtain a desire of a recipient if he or she would like to move down or otherwise revert to the old map. Indeed, the two could be not mutually exclusive—the prompt could ask for both. Note also that in an exemplary embodiment, the device 240 could simply wait for the recipient to engage in the action of changing the focusing. Indeed, in an exemplary embodiment, the teachings detailed herein could be entirely based on the recipient's desires or actions. On an almost opposite side of the spectrum, in an exemplary embodiment, the system could actually obtain data in a passive manner or an inactive manner and determine whether or not it might be a utilitarian time to adjust the focusing. Such exemplary scenarios are described in greater detail below.

Any arrangement that can enable the teachings detailed herein to enhance human life with respect to determining whether or not there should be a map that is progressed and/or regressed can be utilized in at least some exemplary embodiment.

Still, in one of the more simple forms, in an exemplary embodiment, a simple timer is utilized to determine when to prompt the recipient or otherwise make changes. This could be on a set time period, such as a few days or a week or 10 days, etc., or any of the temporal periods detailed herein, and could be a fixed schedule, but also could be on a schedule that is more customized to the recipient, whether such is based on empirical data associated with the past performance of the recipient, or whether such is based on human factors engineering data associated with a recipients demographic or the like. Moreover, the timing could be variable based on performance of the recipient. If the recipient shows aptitude for quickly progressing through maps, the time period could be truncated or otherwise shortened, while the converse could also be the case. Any arrangement of determining when it is utilitarian to prop the recipient to progress or regress in maps can be utilized in at least some exemplary embodiment.

The system 240 can provide a screen that enables the recipient to activate a program that results in the increased focusing of the prostheses. This could be prompted or could be something the recipient chooses to do on his or her own volition without prompting. The screen could provide up arrows and/or down arrows that could permit the recipient to increase or decrease the level of focusing by single increments or by multiple increments if he or she chooses. A "dial a focus" feature to be provided where the recipient dials in the amount of focusing that he or she chooses or the amount of increased or decreased focusing that he or she chooses or something that serves as a proxy representative of the amount or the type of increased or decreased focusing (e.g., a generic concept of focusing levels or a percentage, as opposed to asking the recipient the percentage of return electrical current that is to be permitted to return via neighboring electrodes and the extracochlear electrode, where it is presumed that at least some recipient will find this to be meaningless if not disturbing). Upon receiving such import, the device 240 could be programmed to adjust the focusing portion of the map accordingly, and then implement the adjustment testing or the like through the test interface for the recipient.

Moreover, in at least some exemplary embodiments, the device 240 is configured to enable testing for threshold and comfort levels or otherwise to collect data based on stimulus, or, more accurately, resulting from stimulus applied to the recipient, associated with the threshold and/or comfort levels detailed above. In this regard, device 240 can be configured to automatically implement such testing or the like, at least when prompted by the recipient to do so. The testing could be interactive. The device 240 can be configured to receive input indicative of the recipient responses to given stimulation to determine T and/or C levels, etc. The device 240 can be configured to provide an electronic-based hearing percept that is indicative of a sound that would be captured by the microphone of the hearing prosthesis, but one that bypasses the microphone. Alternatively, and/or in addition to this, the device 240 can be configured to output sounds that will be captured by the microphone, and thus will result in a hearing percept, where the volume of the sound that is outputted can be correlated to the recipient's reaction to the resulting hearing percept that is evoked T and C levels can be developed based on the input indicative of the recipient's reaction.

While embodiments are generally focused on the utilization of the smart device 240, it is again noted that in other embodiments, other types of devices, such as, for example, a laptop or a desktop computer can be utilized. These devices can be placed into signal communication with the prostheses in a wired and/or a wireless matter. Further, it is not necessarily the case that true computing devices are utilized. In an exemplary embodiment, an interactive TV system could be utilized. In an exemplary embodiment, there could be a "prosthesis channel," or a DVD could be played, where input is provided into the entertainment system/the entertainment system provides the stimulation.

Moreover, while embodiments have focused on a remote device that is remote from the prosthesis, in other embodiments, the device that controls or otherwise adjusts the focusing is based entirely in the prostheses. The input indicative of the recipient response could also be input directly into the prostheses. In an exemplary embodiment, a pre-recorded/pre-determined testing material can be prepared in the form of sounds of the like that can be played by any noisemaking device, such as, for example, the prosthesis itself, a television or a CD player or an MP3 player, etc., and the sound would be communicated to the hearing prosthesis, and thus the interest he sees would evoke a hearing percept, and the recipient could then provide input into the hearing prostheses indicative of what the recipient perceives. This could be done vocally or by manual input into a data interface of the prostheses. Indeed, in an exemplary embodiment, the sound could have embedded therein at a potentially supersonic frequency a code that the prosthesis can decipher so that the prosthesis understands the type of sound/level of sound that is being produced. Alternatively, and/or in addition to this, the code could be within the 20 Hz to 20 kHz band, but the prosthesis could be configured to not evoke a hearing percept within the narrow frequency brand of the code when testing is commenced. Any arrangement that can enable the recipient to self-test or otherwise fine-tune by himself or herself the prosthesis after the adjustment of the focusing is made can be utilized in at least some exemplary embodiments. Thus, in an exemplary embodiment, the system is configured to enable the recipient to self-test/self-diagnose an efficacy of the increased focusing.

To be clear, it is also the case that in at least some exemplary embodiments, the adjustment focusing are executed entirely utilizing the hearing prostheses. Thus, the systems under discussion include the system of FIG. 2A for example, or the hearing prosthesis by itself, or a system that includes a remote server and the like, etc.

In this regard, and an exemplary embodiment, the system is configured to enable the recipient to increase focusing in at least W different increments, where W equals n or n times 2 or 3 or 4 or 5 or 6 or 7 or any value or range of values therebetween in integer increments.

In view of the above, it can be seen that the device configured to control stimulation includes at least one hearing prosthesis map, and that the system is configured to at least one of operationally adjust the map or operationally replace the map with a new map to adjust the focusing. The system also enables the recipient to do either or both.

Consistent with the concepts of being able to bail out or otherwise refuse a given change to focusing, the system can be configured to store one or more previous maps and/or preadjusted maps having a lower level of focusing relative to the adjusted/replacement maps, and the system is configured to enable reversion to the stored one or more previous maps and/or preadjusted maps for at least temporary use and/or testing purposes. In this regard, in an exemplary embodiment, if the recipient determines that the level of focusing provides too much stimulus to him or her or otherwise is too difficult to utilize or simply does not like the new focusing, the recipient can have the system revert to the prior focusing regime. In an exemplary embodiment, the prosthesis can have an input sub-system that causes the prior map to be reloaded or otherwise used. In an exemplary embodiment, there could be an application on the device 240 that when activated, wirelessly transfers the old map to the prosthesis and forces the prosthesis to accept that map. In an exemplary embodiment, the recipient could simply state out loud a control command that would be picked up by the microphone of the prosthesis and interpreted as a command to default back to the prior map (or to a "safe map" for that matter, which is always stored in the prosthesis, which could correspond to, for example, simple monopolar stimulation—note also that the map per se need not necessarily be stored—the device could simply be controlled to operate in a given stimulation regime). In such an exemplary embodiment, the system would not necessarily include device 240, but instead could be a system that is entirely based in the hearing prosthesis.

As noted above, focusing and/or T and C level analysis/adjustment is performed at least in some embodiments on a per channel basis. Thus, in an exemplary embodiment, the device configured to control stimulation includes a plurality of stimulation channels. In an exemplary embodiment, there are W stimulation channels, where W equals less than, more than or equal to 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 120, 130, 140, 150, 160, 170, 180, 190, 200, 250, 300, 350, 400, 500, 600, 700, 800, 900, 1,000, 1,250, 1,500, 2,000, 3,000, 4,000, 5,000, 6,000, 7,000, 8,000, 9,000, or 10,000, or more or any value or range of values in integer increments.

In some embodiments, the system is configured to adjust at least a subset of channels less than the total number of channels with respect to focusing (which includes adjusting all channels). In an exemplary embodiment, the number of channels that are adjusted/adjustable equals W or W minus 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 120, 130, 140, 150, 160, 170, 180, 190, 200, 250, 300, 350, 400, 500, 600, 700, 800, 900, 1,000, 1,250, 1,500, 2,000, 3,000, 4,000, 5,000, 6,000, 7,000, 8,000, 9,000, or 10,000, or any value or range of values in integer increments.

In an exemplary embodiment, there is non-transitory computer-readable media having recorded thereon, a computer program for executing at least a portion of a method and/or functionality disclosed herein, that includes code for doing such. The following will be described in terms of such a media, but it is also noted that the following corresponds to the disclosure of a method with or without the media.

An exemplary embodiment includes a non-transitory computer-readable media having recorded thereon, a computer program for executing at least a portion of a method of fitting a sensory prosthesis to a recipient, the computer program including code for enabling recipient controlled gradual transitioning of the prosthesis from less focused stimulation to more focused stimulation. This is distinct from a code that enables only abrupt transitioning of the prosthesis from less focus stimulation to more focused stimulation. This also as distinct from a code that enables only a healthcare professional or a technician or a manufacturer of the prosthesis to transition the device.

In an exemplary embodiment, there is further code for adjusting stimulation intensity levels based on input from the recipient for given focusing regimes, consistent with the disclosure above of the fine tuning of the T and/or C levels. Further, there is code for adjusting a map and/or developing a new map for respective focusing settings of the prosthesis. In an exemplary embodiment, the code enables the audiologist or other healthcare professional or technician to do so, while in other embodiments, the code enables the recipient to do so (which is not mutually exclusive from also enabling another group to do so.

Consistent with the teachings detailed above where the system is interactive with the recipient, there can include an embodiment where the media includes code for obtaining data indicative of recipient perceptions for respective prosthesis focusing regimes.

It is noted that while some embodiments are directed towards utilizing the aforementioned data indicative of recipient perceptions to further adjust the prosthesis, which adjustment can be made in an automated or semiautomated manner, in other embodiments, the data is simply utilized to evaluate what might possibly be done with respect to adjustments. In this regard, it is noted that while in some embodiments, the system can autonomously adjust the prosthesis, based on the data indicative of the recipient's perceptions, in other embodiments, the system passes the data on to a sensory professional who can adjust or otherwise allow adjustment. Still, in at least some embodiments, the code for enabling the recipient-controlled transitioning is code for self-fitting of the prosthesis to the recipient. Further, at least some exemplary embodiments, this code for self-fitting includes code for adjusting stimulation magnitudes of channels after the channels are focused. In some embodiments, the system is configured to limit the amount of adjustment that can occur.

While some embodiments are directed towards utilizing the expertise of a trained audiologist or otherwise a trained sensory professional, in other embodiments, there is code for evaluating an efficacy of results of the gradual transitioning. As with all embodiments disclosed herein, providing that the art enables such, unless otherwise noted, this code can be entirely based on the device 244, the personal computer that is part of the system, or the prosthesis itself. In an exemplary embodiment, the system can provide data indicative of the efficacy to a healthcare professional at a remote location, while in other embodiments, there is additionally code for executing supplemental focusing and/or defocusing based on the evaluation of the efficacy. This can entail code that evaluates the recipient's performance based on inputs associated therewith, which can be passive or active, as described in greater detail below, and automatically develops an adjustment to the focusing regime. In an exemplary embodiment, this can correspond to determining that it is time to move up to the next progression in the map. In an exemplary embodiment, this can correspond to determining that the focusing increase was too aggressive and a prior map should be used or otherwise defocusing should be defocused relative to that which was the case. Again, this can be in predetermined decrements and/or can be based on recipient-controlled decrements, etc. This can be an application on the device 240 that enables the recipient to decrease the level of focusing in steps or the like.

Consistent with the theme of increasing focusing at a rate that is not overwhelming to the recipient, in an exemplary embodiment, the media can include code for limiting a change in focusing to no more than a certain percentage per channel and/or per a number of channels and/or collectively in a single change (this can be mean, median and/or mode). In an exemplary embodiment, the change in focusing is limited to no more than Z percent per channel and/or per a number of channels and/or collectively, where Z is 0.1, 0.2, 0.3, 0.4, 0.5, 0.6. 0.7, 0.8, 0.9, 1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, or 95, or any value or range of values therebetween in 0.01 increments. The number of channels that are limited can be less than, greater than or equal to 10, 15, 20, 25, 30, 35, 40, 45, 50, 55, 60, 65, 70, 75, 80, 85, 90, 95, or 100 percent of the channels.

Moreover, the limitation can be an intelligent limitation, such as a limitation that focuses on, for example, frequencies associated with speech or frequencies not associated with speech, etc. In this regard, there can be utilitarian value with respect to limiting the amount of focusing for frequencies falling within the speech range more than that which would be the case with respect to lower frequencies or higher frequencies. Indeed, in an exemplary embodiment, it is contemplated that some channels will be "maxed out" well before other channels, or at least before other channels with respect to focusing. In this regard, in an exemplary embodiment, it is possible that maximum focus could be applied for certain channels at inception of the actions of increasing the focusing, if not at the time of actual activation of the prosthesis.

Moreover, the teachings detailed herein include identifying channels where the recipient has more difficulty accepting increased amounts of focusing relative to other channels and influencing or otherwise controlling how much a given channel will be focused/how much a given channel will be increased with respect to focusing (or decreased for that matter) based on the aforementioned identification. In this regard, 1 or 2 or 3 or 4 or 5 or 6 or 7 or 8 or 9 or 10 or D percent of channels can have an increase in focusing that is less than, greater than, or equal to 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 120, 130, 140, 150, 160, 170, 180, 190, 200, 250, 300, 350, 400, 500, 600, 700, 800, 900, 1,000, 1,250, 1,500, 2,000, 3,000, 4,000, 5,000, 6,000, 7,000, 8,000, 9,000, or 10,000 percent, or any value or range of values therebetween in 0.1 percent increments relative to an increase of another channel and/or an average (mean, median and/or mode) of 2 or 3 or 4 or 5 or 6 or 7 or 8 or 9 or 10 channels or D percent of channels, where D is any value above or below or the same as 10, 15, 20, 25, 30, 35, 40, 45, 50, 55, 60, 65, 70, 75, 80, 85, or 90 or any value or range of values therebetween in 0.1 increments.

Again, the intelligence regime of increasing can be focused upon certain frequencies relative to other frequencies. In any event, in at least some exemplary embodiments, there are devices, systems, and/or methods that can identify channels that are appropriate for increased levels of increased focusing relative to other channels, and for increasing the level of focusing accordingly.

Some embodiments include variations of implementing the various teachings herein. In one exemplary embodiment, the actions of adjusting the single-channel loudness, sweep and balance activities associated with establishing new C level profiles, the action of determining the level of first hearing for a multichannel stimulus and/or the execution of the sweep and balance at 50% of the dynamic ranges, and work some of the other methods detailed herein, can be executed for some (less than, greater than or equal to 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, or 95 percent or any value or range of values therebetween) or all of the channels in one sitting and/or in a temporal period lasting no more than 1, 1.5, 2, 2.5, 3, 3.5, 4, 4.5, 5, 6, 7, 8, 9, or 10 hours or any value or range of values therebetween in 0.1 hour increments.

In an exemplary embodiment, the individual measurements on any of the aforementioned numbers of channels can be executed in one sitting and/or with respect to the aforementioned temporal period. This could include, for example, determining the single-channel loudness and/or the individual T level measurements. Multichannel measurements, such as the sweep and balance of new C level profiles and/or the sweep and balance at the 50 percentile of the dynamic range could be executed at a later date in another sitting, such as within the aforementioned temporal periods but after the first temporal period.

Further, in an exemplary embodiment, each of the testing steps could be executed in separate settings and/or within the aforementioned time periods. In an exemplary embodiment, the single-channel loudness actions could be executed in a single sitting and/or within the aforementioned time periods, then the sweep and balance of new C level profiles could be executed in a single sitting and/or within the aforementioned time periods, and then the determination of the level of first hearing for a multichannel stimulus could be executed in a single sitting and/or in the aforementioned time periods and/or the sweep and balance at 50 percentile of the dynamic range could be executed in one sitting and/or within the aforementioned time periods.

Further by way of example, the loudness measurements could be completed in one sitting and/or within the aforementioned time periods, such as the actions associated with determining single-channel loudness in the sweep and balance of new C level profiles, and then the completion of the soft sound measurements could be executed in another sitting and/or within the aforementioned time periods.

It is further noted that any of the individual species of actions and/or genus of actions can be executed over multiple sittings or within multiple temporal periods. By way of example only and not by way of limitation, in an exemplary embodiment, the single-channel loudness setting actions can occur over multiple test sessions (sittings) and/or over multiple temporal periods corresponding to those previously detailed. In an exemplary embodiment, there could be threshold requirements that must be met before moving on to the other actions. For example, there could be a limitation on moving on to the sweep and/or balance of new C level profiles were such is done only after all of the channels are completed or after a certain number of percentage of the channels have been completed and/or only after a certain number or all of the "significant" channels relative to other channels or otherwise channels of interest have been completed.

In an exemplary embodiment, only after all of the single-channel loudness actions have been addressed, does the method move on to the sweep and balance and/or only after the sweep and balance has been executed for a predetermined number of channels, which could be all channels, does the method move on to the completion of individual T level measurements and/or the beginning part of the determination of the individual T level measurements (the pre+5 CL testing), which can be executed in one or multiple test sessions, etc., as is the case with all of the actions detailed herein in some embodiments. Then, only after the T level measurements are achieved, or at least the first part thereof, does the method move on to the remainder of the actions associated with determining the level of first hearing for multiple channel stimulation (e.g., the +5 CL testing). And then, only after all of actions associated with determining the level of first hearing or executed, though the method move on to the sweep and balance at the 50 percentile of the dynamic range, which can be executed in a single sitting work over multiple sittings as is the case with all of the actions detailed herein.

In an exemplary embodiment where there are multiple sittings, in an exemplary embodiment the time period between the beginning of the first sitting and the end of the last sitting can be limited or otherwise predefined to trigger certain actions. By way of example only and not by way of limitation this can have utilitarian value with respect to ensuring that the initial changes or settings do not become "old" or otherwise outdated because the process is taking too long (as would be defined based on empirical and/or statistical data for a given demographic, for example). In an exemplary embodiment, the methods could be limited to, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 40, 45, 50, 55, 60 or more days or any value or range of values therebetween in 1 hour increments, from beginning to end, where if the limitations are exceeded, the process would have to be started over or some other action would be utilitarian to be taken, such as increased refinement of the actions associated with the later actions, etc.

It is noted that in at least some exemplary embodiments, the systems that are utilized to implement the teachings detailed herein can have varying degrees of sophistication. By way of example only and not by way of limitation, in an exemplary embodiment, progress can be displayed or otherwise provided to the recipient on tasks and/or steps that are complete. This could be, for example, a bar chart or the like displayed on the display 242 of the device 240, and/or could be in the form of a synthesized speech provided to the recipient indicating status, which could be evoked by the hearing prosthesis. In an exemplary embodiment, certain functionalities could be locked and/or unlocked depending on the state of the recipient and/or the status of the recipient's progress through various actions according to the teachings detailed herein. This can prevent premature adjustments or actions that otherwise might occur in the absence of such. By way of example, functionality can be unlocked as the recipient progresses through the steps. If completing a task and/or a step over several sessions is the case, again, there can be limitations as to the time allowed from the first session to the last session, or at least limitations on opening up the functionality based on temporal requirements. That is, the system can be configured to prevent the recipient from activating certain functionalities if certain pre-requirements are not met. (While the above has focused on temporal periods, it is noted that functionality locking and/or unlocking can also be based on other data points, such as, for example, performance, input from others (parents, caregivers, etc.), age, time of day, time of week, etc.). It is also noted that in some exemplary embodiments, the system can be configured to automatically bring in or request information from the audiologist or other sensory professional or healthcare professional. By way of example only and not by way of limitation, the system could be configured to lock a given functionality until a professional affirmatively unlocks that functionality. For example, if the aforementioned temporal periods are exceeded, the system could automatically contact a healthcare professional and request information is whether or not the recipient should be permitted to proceed even though a precondition has not been met. Alternatively, the functionality could be locked irrespective of given preconditions, and the audiologist must affirmatively unlock these functionalities based on a prompt from the system.

In an exemplary embodiment, if various conditions precedent are not met, such as the aforementioned temporal periods, the system could default to a precondition, such as requiring testing/evaluation to start from the beginning. By way of example, if the last session surpasses a predetermined time frame, the testing would be required to start over from the beginning and/or would be required to start over at another point in the testing, etc. Alternatively, and/or in addition to this, some of the testing would be required to be repeated while other testing might not necessarily be required to be repeated.

Embodiments also include a reward regime and/or another type of regime for completing tasks and/or steps. Moreover, a game interface or the like can be utilized to make measurements easier/more intuitive for the recipient or otherwise to make the process less painful or more enjoyable. This can have utilitarian value with respect to children in at least some exemplary embodiments.

Any arrangement of increasing compliance or otherwise encouraging the recipient to utilize the teachings detailed herein or otherwise ensuring the efficacy or otherwise increasing the efficacy of the teachings detailed herein relative to that which would otherwise be the case can be utilized in at least some exemplary embodiments.

In an exemplary embodiment, after the development of the new map, there is commenced an execution of testing of performance of the new map. Evaluation of performance with the new map can be done, in some embodiments, acutely and/or after a period of acclimation and/or after a specified temporal period, such as at least after 1, 2, 3, 4, 5, 6, 7, 8, 9, 10, 11, 12, 13, 14, or 15 hours, or days, or weeks, or more. Testing could be administered using the test interface (such as that which is an application in the recipient's mobile device and/or can be personal computer based, whether such is the recipient's or the clinician, etc.) and could be performed via direct connect or in a clinic's sound attenuating booth. Any device, system, and/or method that can enable testing of performance can be utilized in some embodiments.

In an exemplary embodiment, there is audibility testing, which can entail determining whether aided audiometric thresholds with the new map are in a clinically acceptable range, and if not, adjustments or the like can be made to the map which can bring the audiometric thresholds within the clinically acceptable range.

In an exemplary embodiment, speech discrimination tests are implemented, which can include, by way of example only and not by way of limitation, word and/or sentence in noise and/or in quiet. Based on the results of the tests, modifications to the map could be made, which modifications may not necessarily result in the consistency across the channels that were previously achieved via the aforementioned fine-tuning processes detailed herein and/or variations thereof or other embodiments that can result in utilitarian adjustments to the map. Still further in some embodiments, alternatively and/or additionally, other measures of hearing performance can be tested, such as, for example, dimensions of hearing performance beyond speech. By way of example only and not by way of limitation, such could be assessed using psychophysical tests of spectral resolution, such as spectral ripple and/or musical tests. Again, as a result of such tests, adjustments to the map can be made so as to improve the spectral resolution as such is desired.

Still further, the valuations of channel interactions can be implemented. Indeed, channel interactions are one method to determine a level of focusing needed to achieve a desired result, such as the determination of the maximum level of focusing to achieve optimization of the ultimate map. In one embodiment, as described above with respect to the algorithm FIG. 7, channel interactions are measured between neighboring probe and perturber channels and the focus of the channels can be adjusted until the interaction is minimized or otherwise reduced to a value that is utilitarian. When the minimum interaction point for each channel is reached and/or when a desired interaction point for each channel is reached, the focusing is at the optimal level and/or is at a utilitarian level. Increased focusing from the optimal level would introduce more channel interactions, and thus it may not necessarily be utilitarian to continue focusing. Indeed, in an exemplary embodiment, channel interactions can be evaluated and otherwise utilized as a determiner to stop further focusing adjustments.

Further, in other exemplary embodiments, there is the action of reviewing test results and making recommendations for further fine tuning. In an exemplary embodiment, based on tests, which can occur immediately after the adjustments, or as a result of more long-term testing in the following hours or days or weeks after the increased focusing is implemented, performance can be evaluated, and if it is determined that performance is not the same or better than the performance that was the case with respect to the less focused maps, further fine tuning could be implemented. Alternatively, in an addition of this, even more increased focusing could be called for. Further, focusing of some channels to the exclusion of others could be adjusted. Also, in an exemplary embodiment, the prior map could be reverted to and the progress of mapping could be held steady until the recipient further matures or otherwise undergo some form of training or remedial education vis-à-vis utilizing the prostheses, etc.

Corollary to the above example is that the benefits of the new map can be evaluated. By way of example only and not by way of limitation, the results across all maps can be compared to determine the level of focusing that provides better performance relative to other levels of focusing. To be clear, it is possible that some levels of focusing simply do not provide utilitarian results beyond that which would be the case with respect to less focusing. In such scenarios, a clinician or other healthcare professional or even the system could automatically make a recommendation to continue transition workflow and/or to utilize a previous map that is determined to have a better performance. Indeed, in some extreme cases, a determination can be made based on the comparisons of performance that the recipient has "maxed out" with respect to improvements associated with further focusing maps. In such a scenario, it could be utilitarian to declare a moratorium on further focusing forever and/or for a given temporal period and/or until another event occurs. Still further, in such a scenario, remedial activities or additional activities could be undertaken by the recipient to improve the likelihood that further focusing will provide utilitarian results beyond that which is the case with respect to the less focused maps. By way of example only and not by limitation a recipient might be instructed to take lip reading classes and/or might be instructed to practice utilizing the hearing prosthesis by listening to sounds of more complex nature or otherwise engaging in training exercises with the prosthesis.

It is noted that in at least some exemplary embodiments, the system could automatically or semi-automatically make the above-noted evaluations based on test results or the like. Still further, again as will be described in greater detail below, the system can actively and/or passively obtain data while the recipient is utilizing hearing prostheses and determine whether or not the recipient is experiencing increased benefit from the new map relative to that which was the case with respect to the prior maps. Also, at least some exemplary embodiments include raw recipient self-evaluation. The recipient might simply declare that he or she does not like the new map and that could be that for that map. Of course, a graduated scale of dislike could be implemented, and such could be combined with counseling from a healthcare professional or the like, but in the end, the recipient could simply declare no joy and stop use of the map and have the system implement one of the older maps.

Further, recipient assessment of the new map is optional and could be done acutely or after a period of acclimation or both. The recipient could be prompted to try the new map with various inputs including but not limited to environmental sound presented via the processor microphone, recorded speech, live speech from familiar talkers, and/or music. Paired comparison testing could be administered. The user would elect to keep the new map or revert back to the parent map in some embodiments. Optionally, the recipient will be prompted for feedback on the new map and, if applicable, the reasons why it was not kept. This latter feature can be utilized for data collection purposes and/or for building a database on that given recipient or on a demographically significant group of recipients so that future activities associated with focusing can be more utilitarian than that which was otherwise the case.

In view of the above, it can be seen that the various actions detailed herein can be repeated on a regular basis such as a present time interval and/or on a non-regular basis such as on a user-controlled were user desired basis, which repetitions can be determined by the clinician and/or the individual recipient or otherwise a care giver of the recipient.

Figure 14:
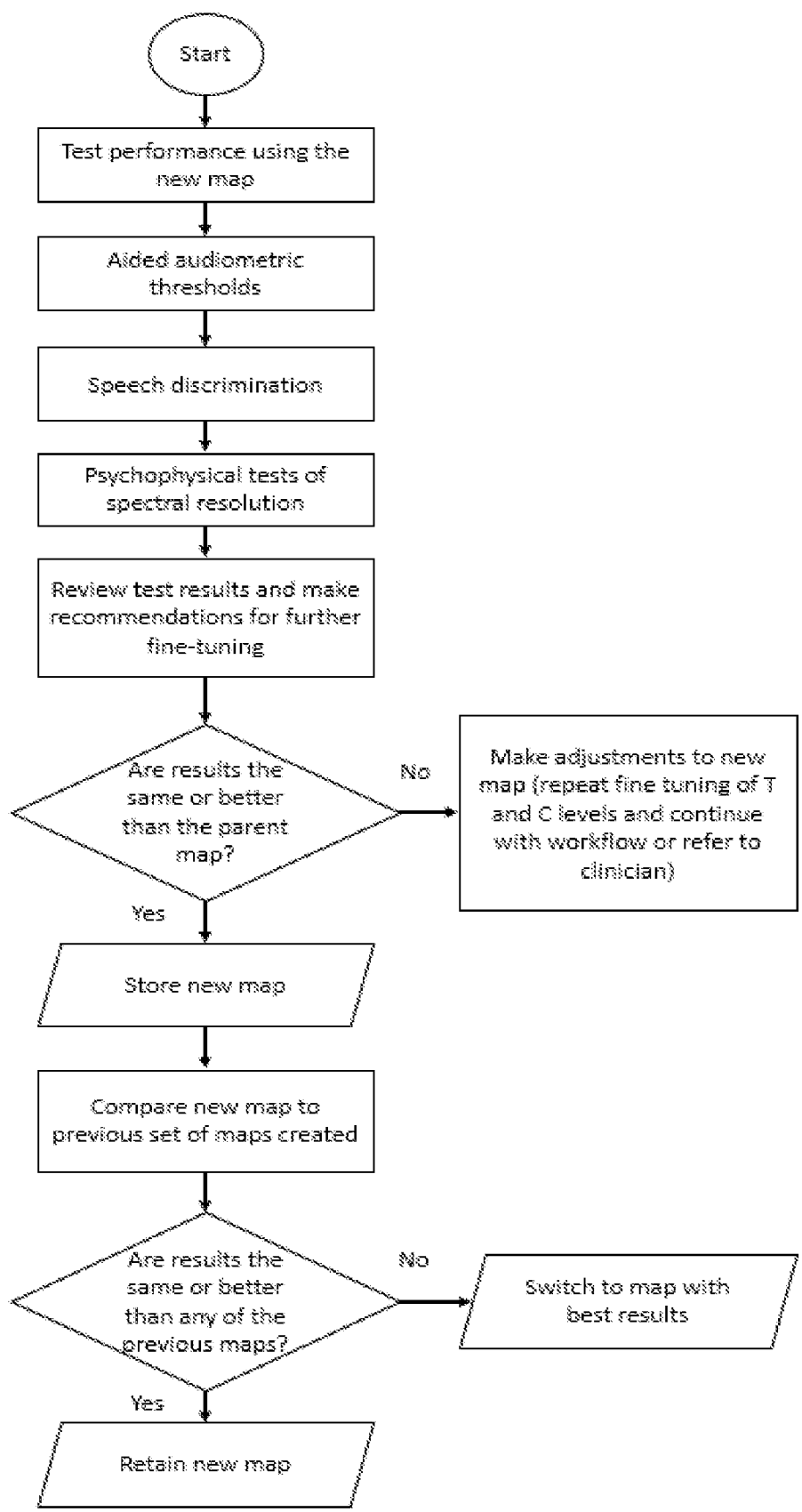
Figure 15:
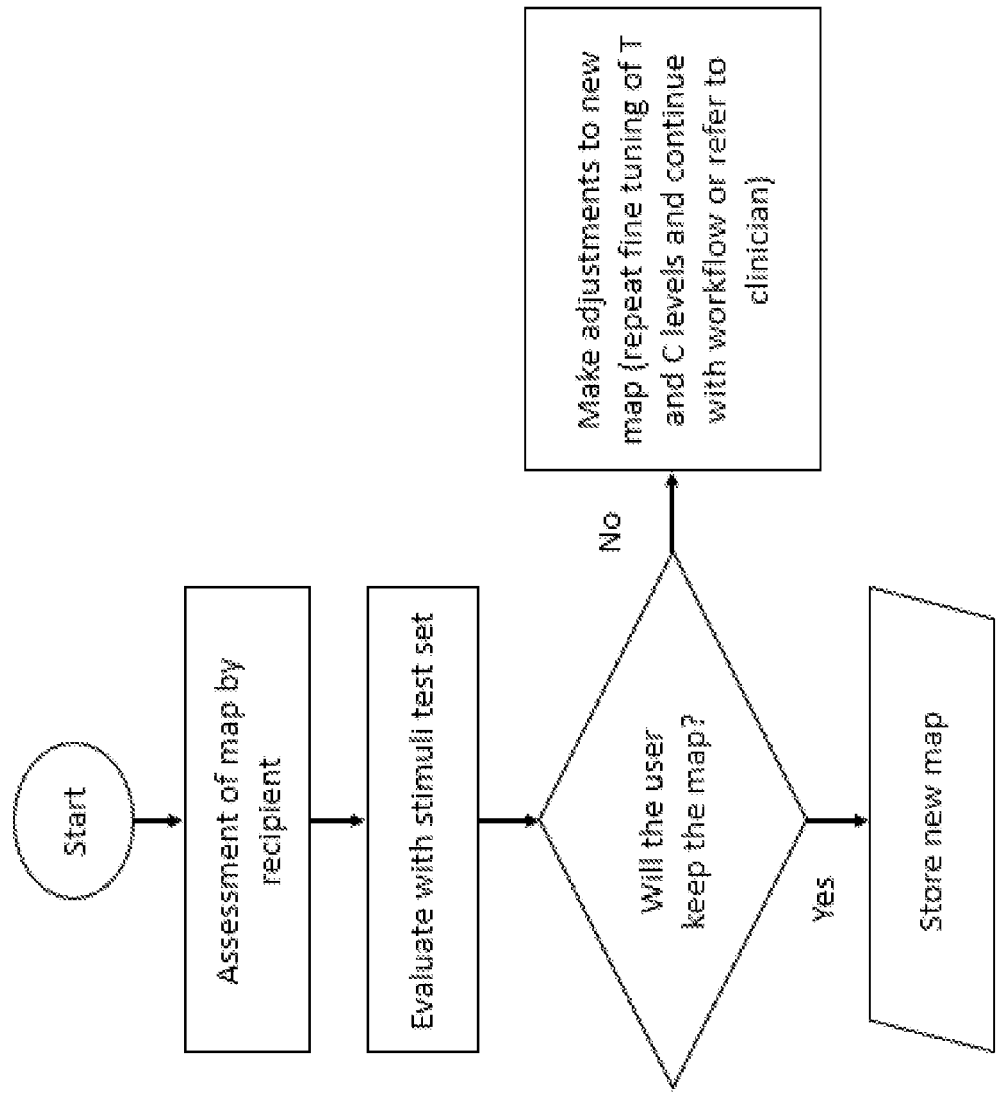

FIGS. 14 and 15 present exemplary flowcharts for exemplary methods that could be executed to evaluate the efficacy of the new focused map and/or the tuning to the T and C levels for that map and/or determine whether such should ultimately be maintained or discarded. Any one or more of the method actions presented in these flowcharts can be executed in any order and/or any one or more of those actions can be omitted (as is the case with all of the methods detailed herein—any action can be executed before and/or after any other action and/or any action can be omitted unless otherwise noted).

Figure 16:
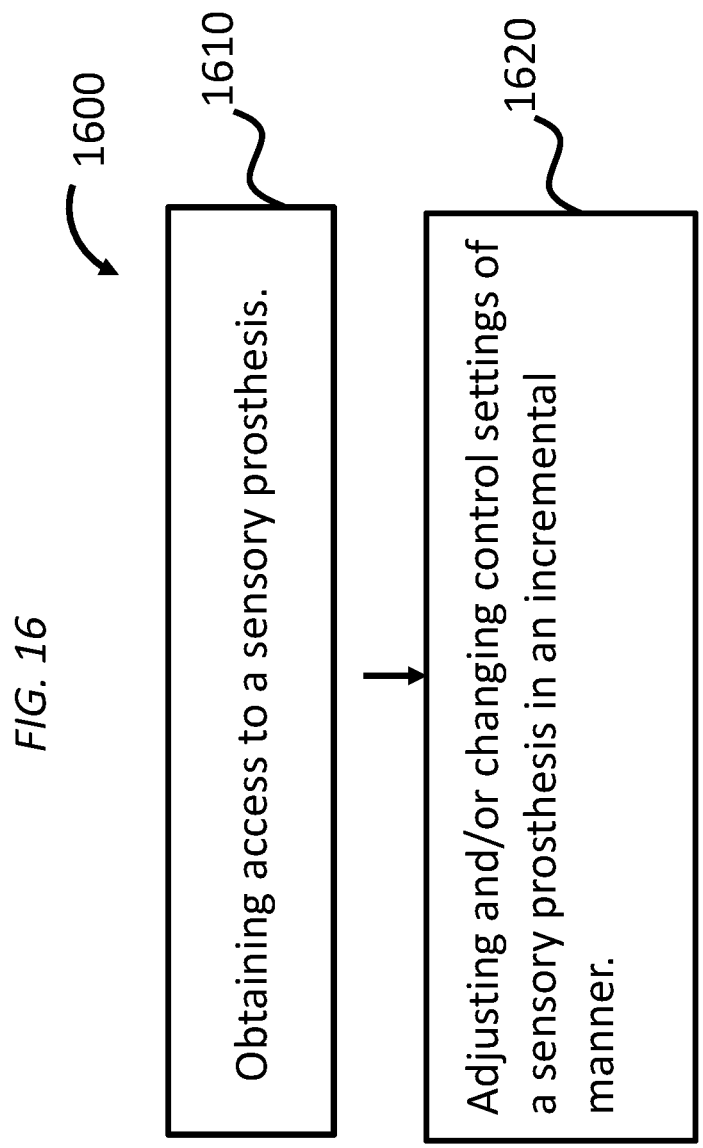

FIG. 16 presents another exemplary algorithm for an exemplary method. Method 1600 includes method action 1610, which includes obtaining access to a sensory prosthesis. Method further includes method action 1620, which includes adjusting and/or changing control settings of the sensory prosthesis in an incremental manner. In an exemplary embodiment, the action of adjusting and/or changing the control settings in the incremental manner reduces the risk of (which includes avoids) overstimulation of the recipient relative to that which would be the case in the absence of the limitation of the incremental manner. That said, in an alternate exemplary scenario, the action of adjusting and/or changing the control settings in the incremental manner results in overstimulation to the recipient. In an exemplary embodiment, the adjustments are refined (e.g., the level of focusing is reduced, T and/or C levels are adjusted, etc.) or otherwise voided upon determination of such an occurrence.

In an exemplary embodiment of this method, the incremental manner includes focusing the prosthesis to have more focus than that which was previously the case but less focus than a maximum focus possible by the prosthesis, consistent with teachings detailed above. That said, in some other exemplary embodiments, the incremental manner includes focusing the prosthesis to have more focus than that which was previously the case and also a focus that is the maximum possible. Thus, in an exemplary embodiment of this method, the incremental manner includes focusing the prosthesis to have more focus than that which was previously the case and less focus than a maximum focus possible by the prosthesis or the maximum amount of focus possible.

In an exemplary embodiment of the method 1600, there is further the action of obtaining data indicative of an efficacy of the adjusted and/or changed control setting, and further adjusting and/or changing the control setting based on the obtained data for remedial purposes. This as opposed to, for example, further adjusting and/or changing the control settings with respect to the progress of maps concept detailed above. Here, there is an identified deficiency with respect to the map, and this deficiency is attempted to be addressed for remedial purposes. Consistent with the teachings detailed herein where at least some exemplary embodiments are entirely or almost entirely recipient controlled, the action of adjusting and/or changing is executed entirely by a recipient of the prosthesis. This can also be the case with respect to the aforementioned changes for remedial purposes. That said, in another embodiment, an audiologist/sensory professional or other healthcare professional steps in and is in control of the aforementioned changes.

At least some exemplary embodiments of the method 1600 include the action of adjusting a magnitude of stimulation associated with the adjusted and/or changed control settings, wherein the action of adjusting and/or changing the control settings and the action of adjusting the magnitude is executed entirely by a recipient. Again, in at least some exemplary embodiments, a sensory professional or other healthcare professional executes at least some of the methods detailed herein.

By way of example only and not by way of limitation, with respect to the aforementioned method actions detailed herein, at least some embodiments include going through at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 80, 90, or 100 or more cycles of the methods detailed herein or any value a range of values therebetween in integer increments (n could equal any of the numbers just detailed) without active and/or without passive healthcare professional involvement. In an exemplary embodiment, the healthcare professional could be involved every five or 10 or 15 or 20 or more cycles. The healthcare professional may never be involved except when there is a problem identified by the recipient and/or based on data analysis that is executed by the system automatically. Still further, the healthcare professional might only be passively involved by reviewing the progress and/or the results of testing or the like.

Consistent with the teachings detailed herein with respect to utilizing device 240 or the like, so as to enable recipient based/recipient-controlled adjustments, in an exemplary embodiment, method 1600 is executed using a smart device that is in communication with a hearing prosthesis. In an exemplary embodiment, the smart device is a handheld smart device. In an exemplary embodiment, the action of adjusting and/or changing control settings of the sensory prosthesis to increase focusing in an incremental manner is executed at least n times by the recipient, whether or not such is serial. In this regard, it is possible that an intervening method action or multiple intervening method actions can entail adjusting and/or changing control settings of the sensory prosthesis such that the focusing is decreased, consistent with scenarios of reversing or otherwise reducing the amount of focusing upon a determination that a level of focusing provides too much stimulation or otherwise does not provide efficacious results. That said, in an exemplary embodiment, the increase in focusing occurs at least n times in a serial manner without having to revoke or otherwise reduce the focusing.

Still, in an exemplary embodiment, there is an action that entails adjusting and/or changing the control settings in an incremental manner that results in recipient perceived overstimulation. In an embodiment, remedial action takes place upon such identification.

Consistent with the teaching detailed herein, the prosthesis that is the subject of method 1600 can be a prosthesis that has a plurality of stimulation channels, such as any of the numbers detailed herein. Further, the action of adjusting and/or changing the control settings in the incremental manner includes adjusting a stimulation of at least most of the stimulation channels. Also, the method includes adjusting a magnitude of stimulation of at least most of the stimulation channels after adjusting and/or changing the control settings so that a perceived magnitude of a real-world stimulus having a magnitude is at least effectively the same across the at least most of the stimulation channels.

An exemplary embodiment can reduce barriers to focused multipolar stimulation fitting implementation by lifting the burden of fitting off the clinics or otherwise transferring some actions away from the clinics. Clinics could map as they are used to/used devices/systems and/or methods that are used and have been used for monopolar stimulation fitting, rather than use a different mapping technique to fit a focused map. Then the recipient would then transition to a focused map over time, in some embodiments, in an autonomous manner relative to the clinic. This process could take place remotely (with the optional involvement of a remote clinician) or could be performed in a clinic. Progressively transitioning from one stimulation mode to another can result in a database of maps for each subject, ranging from fully monopolar stimulation to fully focused stimulation. In an exemplary embodiment, the system 210 or any other system that can have utilitarian value with respect to implementing the teachings detailed herein can log or otherwise record data throughout the process and/or at key portions of the process. In at least some exemplary embodiments, this can provide a high level of utilitarian data that could be analyzed in a number of different ways for various utilitarian results. For instance, in an exemplary embodiment, it can enable a healthcare professional or entity associated with healthcare or otherwise utilizing the hearing prosthesis to track the changes in current level as a function of the degree of focusing and/or to investigate which levels of focusing are optimal for each region in the cochlea. Accordingly, exemplary embodiments include logging data utilizing the systems detailed herein with respect to one or more or all of the actions that are taken with respect to fitting the prostheses, which data can then be transmitted to or otherwise obtained by an entity that can evaluate the data to improve future fittings for other recipients and/or a given recipient. Based on this data, proposed adjustments to the control settings can be predetermined and utilized to fit the prosthesis relative to other types of adjustments that might be made. By way of example, instead of an even incremental approach to the amount of current that flows through the ground electrode, a nonlinear approach might be more useful with respect to reducing the time to achieve the optimum focusing or otherwise reducing the number of failed attempts to refine the fitting of the prosthesis.

Exemplary embodiments can include collecting transimpedance data at regular intervals and/or non-regular intervals. An exemplary embodiment associated with the utility of such can enable an entity to determine when the recipient has stabilized vis-a-vis any associated trauma or reaction or adaptation to the implant. In an exemplary embodiment, this can provide information about the underlying physiological processes following implantation, which can be analyzed to improve fitting and/or implantation efforts for future recipients. Additionally, tracking performance as a function of focusing can be executed. This can have utilitarian value with respect to determining parameters of monopolar and/or multipolar stimulation and focusing that are best for certain listening situations as compared to other situations. For example, in an exemplary scenario, the data can be analyzed, and based on the data, correlations between various levels of focusing and the utilitarian value of such for a given listening scenarios/hearing scenarios can be made. In an exemplary embodiment, the analysis can yield determinations that a first level of focusing is utilitarian/more utilitarian for everyday listening relative to other levels of focusing (which could be higher and/or lower than other types of focusing that could be possible by the device), and a second level of focusing is utilitarian for speech and noise situations (which could be higher and/or lower than other types of focusing that are possible by the device, which could be higher or lower than the level of focusing that is utilitarian with respect to everyday listening and/or any of the other listening/hearing scenarios detailed herein), and a third level of focusing that is utilitarian for music (which can be higher and/or lower than other types of focusing that are possible by the device, which can be higher or lower than the level of focusing that is utilitarian with respect to the other types of hearing/listening scenarios detailed herein), etc.

Accordingly, an exemplary embodiment includes collecting data and creating a plurality of maps that can be engaged based on a different listening/hearing scenario determined by the system and/or determined by the recipient, and the system could utilize a given map having a given level of focusing for that listening/hearing situation. All of this can be based on data that is collected utilizing the systems, which data collection can be passive and/or active in accordance with the teachings detailed herein.

In a utilitarian embodiment, the workflow can be used to transition listeners from monopolar stimulation to focused monopolar stimulation. That said, in at least some exemplary embodiments, the teachings detailed herein can be utilized to transition from monopolar stimulation and/or bipolar stimulation to tripolar or partial tripolar stimulation.

In view of the above, at least some exemplary embodiments can provide a modicum of relief to the difficulties associated with switching from one stimulation mode to another, at least for recipients that have more difficulty adapting if the perceived change is abrupt. The teachings detailed herein can alleviate or otherwise reduced and/or eliminate the abruptness of a change in the focusing, or at least the perceived abruptness of a change in the level of focusing. In an exemplary embodiment, the teachings detailed herein can reduce the number of rejections of a given map relative to that which would be the case in the absence of the utilizations of the teachings detailed herein, all other things being equal. In an exemplary embodiment, for a statistically significant group of similarly situated recipients, the percent reduction with respect to rejection of maps is at least F percent for those that utilize the teachings detailed herein relative to those that do not, all other things being equal, where F can be 10, 15, 20, 25, 30, 35, 40, 45, 50, 55, 60, 65, 70, 75, 80, 85, or 90 or any value therebetween in integer increments. In an exemplary embodiment, the statistically significant group is a group of people falling within the 40 to 60 or 35 to 65 or 30 to 70 or 25 to 75 percentile human factors engineering people with respect to a given sensory deficiency.

In view of the above, it can be seen that in at least some exemplary embodiments, there are devices, systems, and/or methods of gradually transitioning from a monopolar focused regime to a more focused regime, such as a focused map, by providing a recipient with progressively more focused maps in a serial or non-serial manner. The teachings detailed herein, in some embodiments, that include the progressive transition between stimulation modes could increase acceptance of maps that could provide listeners with increased spectral resolution and therefore hearing performance. At least some exemplary embodiments include processes that are individualized to a given recipient, and thus can enable, for example, variability in the rate of transition, testing location (at home using or in the clinic), and map evaluation metrics, to maximize the potential benefit across the implanted population, relative to that which would otherwise be the case in the absence of the teachings detailed herein.

Exemplary embodiments include passive collection of data to validate or otherwise indicate the efficacy and/or the level of stimulation provided by the new maps. In an exemplary embodiment, the microphone of device 240, for example, or the microphone of the hearing prostheses for that matter, could collect sound data and analyze such to determine how well or how unwell the recipient is performing with a given new map. For example, if the recipient is frequently asking a speaker to repeat himself or herself at a rate that is statistically higher than that which was the case prior to the increase in focusing, the system could prompt the recipient to reduce the level of focusing. Alternatively, if the increase is within a statistically expected amounts, and then the number of "repeat requests" reduces according to a statistically expected trend, upon that reduction reaching a certain threshold, the system could automatically prompt the recipient for increased focusing.

Moreover, it is not necessarily the case that the microphone is actually capturing sound data. The data that could be collected by the system could be coil on/off time. That is, if there is an increase in the lack of the utilization of the hearing prostheses immediately after additional focusing, such could indicate that the focusing was too extreme, and hence there could be an automated prompt to defocus, which the recipient could accept or reject. Alternatively, the amount of increased coil on/off time could be within a statistically expected range, and then over time, the amount of on/off time could decrease according to a statistically expected trend, whereupon the decreased reaching a certain threshold, the system can determine that it is time to increase the focusing, because the recipient has acclimated him/her self to the new focusing.

Moreover, while the embodiments detailed above have focused (no pun intended) on the concept of the system automatically prompting the recipient and asking for permission to make a change, in an alternative embodiment, the system could automatically make the change without input from the recipient. Still further, in an exemplary embodiment, the system could automatically notify an audiologist of the collected information or even of a determination that the system is made with respect to how well or unwell the recipient is progressing, and request that the audiologist make the call as to whether or not a change should be made.

In any event, the body carried device and/or the prosthesis itself could be utilized to collect data, and the systems detailed herein can be configured to analyze the data to determine whether or not the new map is efficacious or the like. The data that is captured by the body carried device or the prosthesis can include latent variables which can be utilized as a proxy to evaluate whether or not the map is achieving the desired or otherwise utilitarian results. In this regard, the system can automatically collect and evaluate data to determine such.

Also, the systems can provide the data that is collected whether collected passively and/or actively, whether analyzed or in raw form, to an audiologist or other healthcare professional, who then can evaluate the data and determine the utility of the new map or the like.

Figure 17:
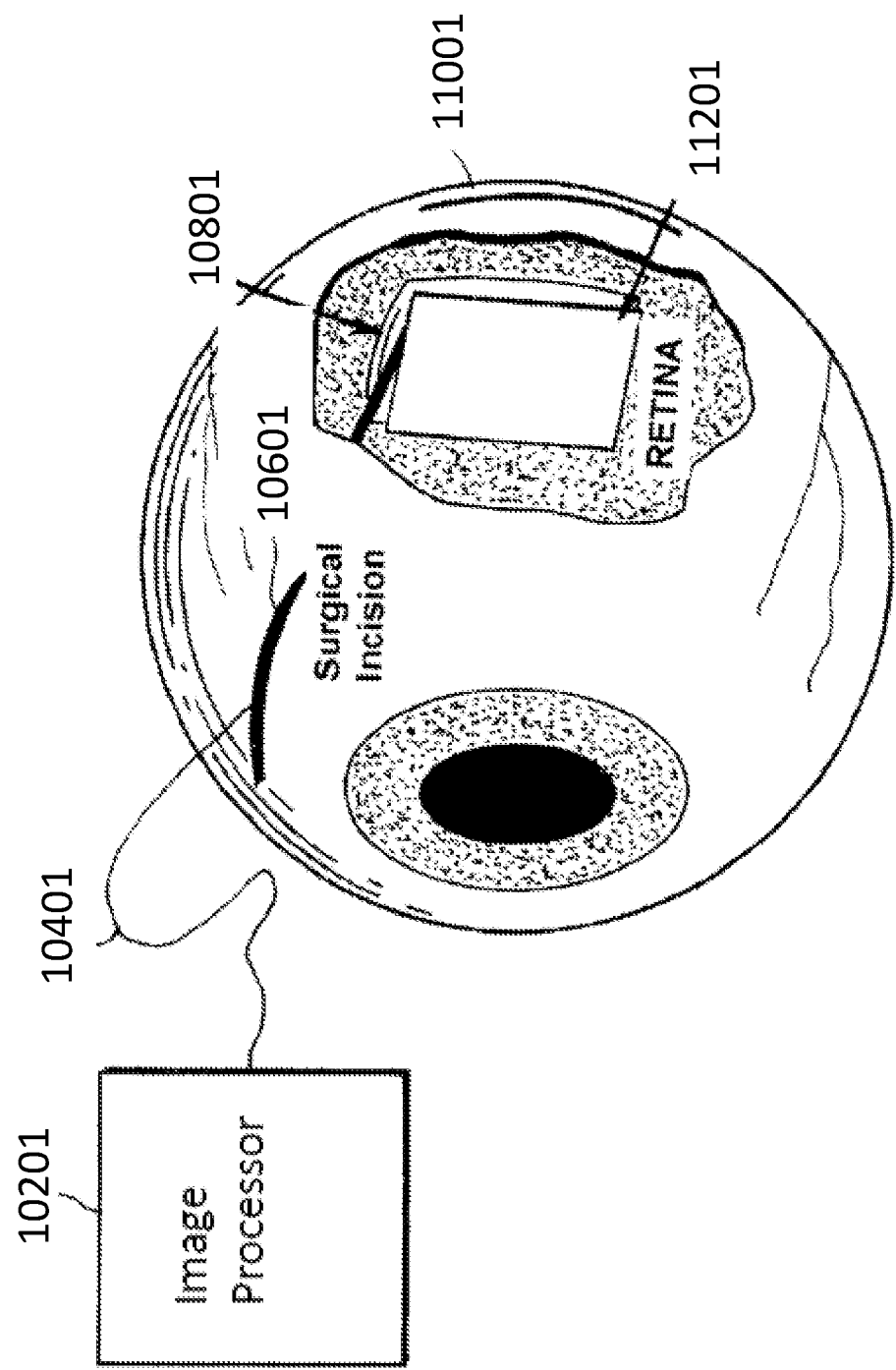
FIG. 17 presents an exemplary sight prosthesis.

FIG. 17 presents an exemplary embodiment of a neural prosthesis in general, and a retinal prosthesis and an environment of use thereof, in particular, the components of which can be used in whole or in part, in some of the teachings herein. In some embodiments of a retinal prosthesis, a retinal prosthesis sensor-stimulator 10801 is positioned proximate the retina 11001. In an exemplary embodiment, photons entering the eye are absorbed by a microelectronic array of the sensor-stimulator 10801 that is hybridized to a glass piece 11201 containing, for example, an embedded array of microwires. The glass can have a curved surface that conforms to the inner radius of the retina. The sensor-stimulator 108 can include a microelectronic imaging device that can be made of thin silicon containing integrated circuitry that convert the incident photons to an electronic charge. An image processor 10201 is in signal communication with the sensor-stimulator 10801 via cable 10401 which extends through surgical incision 00601 through the eye wall (although in other embodiments, the image processor 10201 is in wireless communication with the sensor-stimulator 10801). The image processor 10201 processes the input into the sensor-stimulator 10801 and provides control signals back to the sensor-stimulator 10801 so the device can provide processed output to the optic nerve. That said, in an alternate embodiment, the processing is executed by a component proximate with or integrated with the sensor-stimulator 10801. The electric charge resulting from the conversion of the incident photons is converted to a proportional amount of electronic current which is input to a nearby retinal cell layer. The cells fire and a signal is sent to the optic nerve, thus inducing a sight perception.

The retinal prosthesis can include an external device disposed in a Behind-The-Ear (BTE) unit or in a pair of eyeglasses, or any other type of component that can have utilitarian value. The retinal prosthesis can include an external light/image capture device (e.g., located in/on a BTE device or a pair of glasses, etc.), while, as noted above, in some embodiments, the sensor-stimulator 10801 captures light/images, which sensor-stimulator is implanted in the recipient.

In the interests of compact disclosure, any disclosure herein of a microphone or sound capture device corresponds to an analogous disclosure of a light/image capture device, such as a charge-coupled device. Corollary to this is that any disclosure herein of a stimulator unit which generates electrical stimulation signals or otherwise imparts energy to tissue to evoke a hearing percept corresponds to an analogous disclosure of a stimulator device for a retinal prosthesis. Any disclosure herein of a sound processor or processing of captured sounds or the like corresponds to an analogous disclosure of a light processor/image processor that has analogous functionality for a retinal prosthesis, and the processing of captured images in an analogous manner. Indeed, any disclosure herein of a device for a hearing prosthesis corresponds to a disclosure of a device for a retinal prosthesis having analogous functionality for a retinal prosthesis. Any disclosure herein of fitting a hearing prosthesis corresponds to a disclosure of fitting a retinal prosthesis using analogous actions. Any disclosure herein of a method of using or operating or otherwise working with a hearing prosthesis herein corresponds to a disclosure of using or operating or otherwise working with a retinal prosthesis in an analogous manner.

Various devices, systems, and methods exist that enable the teachings detailed herein. These can be included in the hearing prosthesis and/or the remote devices by way of dedicated specific circuitry added thereto, or by way of modifying the existing circuitry thereof (e.g., reprogramming the existing processors, etc.).

In an exemplary embodiment, one or more of the devices and/or systems and/or subsystems, etc., disclosed herein, and variations thereof, include a processor and/or a chip, which processor of can be a standard microprocessor supported by software or firmware or the like that is programmed to execute one or more of the actions and functionalities herein. The processor can include input and/or output connections. By way of example only and not by way of limitation, in an exemplary embodiment, the microprocessor can have access to lookup tables or the like having data and/or can compare features of the input signal and compare those features to features in the lookup table, and, via related data in the lookup table associated with those features, make a determination about the input signal, and thus make a determination, etc. Numeric analysis algorithms can be programmed in the processors, etc., to implement the teachings herein.

It is noted that the teachings detailed herein can be implemented in any processor-based device and/or chip-based device that can enable the teachings herein. In an exemplary embodiment, a sensory prosthesis, such as a hearing prosthesis or a light prosthesis, can be modified by adjusting the circuitry or otherwise providing programming to a given processor so as to enable the teachings detailed herein. Further, an Internet of things-based approach can be utilized. Also, various components and systems and subsystems can be network so that some actions and/or functionalities detailed herein are performed by components that are remote and/or geographically distant from other components. Accordingly, the teachings detailed herein can be implemented utilizing the Internet or landline-based devices or wireless communication system such as cellular phone communication systems, etc. Any of the prostheses and/or medical devices detailed herein can correspond to body worn devices or body carried devices. Again, these body worn or body carried devices can have processors that are programmed to receive input and/or to provide output to implement the teachings detailed herein. In some embodiments, programs personal computers and/or laptop computers and/or personal handheld devices, such as smart phones or smart watches etc. can be utilized to execute at least some of the functionalities and method actions detailed herein.

Embodiments include circuitry structures that can implement any one or more of the teachings and/or functionalities herein. Consistent with the teachings detailed herein, where any one or more of the method actions detailed herein can be executed in an automated fashion unless otherwise specified, and vice versa.

It is noted that any method detailed herein also corresponds to a disclosure of a device and/or system configured to execute one or more or all of the method actions associated there with detailed herein. In an exemplary embodiment, this device and/or system is configured to execute one or more or all of the method actions in an automated fashion. That said, in an alternate embodiment, the device and/or system is configured to execute one or more or all of the method actions after being prompted by a human being. It is further noted that any disclosure of a device and/or system detailed herein corresponds to a method of making and/or using that the device and/or system, including a method of using that device according to the functionality detailed herein. Any action disclosed herein that is executed by the prosthesis 100 can be executed by the device 240 and/or another component of any system detailed herein in an alternative embodiment, unless otherwise noted or unless the art does not enable such. Thus, any functionality of the prosthesis 100 can be present in the device 240 and/or another component of any system in an alternative embodiment. Thus, any disclosure of a functionality of the prosthesis 100 corresponds to structure of the device 240 and/or another component of any system detailed herein that is configured to execute that functionality or otherwise have a functionality or otherwise to execute that method action.

Any action disclosed herein that is executed by the device 240 can be executed by the prosthesis 100 and/or another component of any system disclosed herein in an alternative embodiment, unless otherwise noted or unless the art does not enable such. Thus, any functionality of the device 240 can be present in the prosthesis 100 and/or another component of any system disclosed herein in an alternative embodiment. Thus, any disclosure of a functionality of the device 240 corresponds to structure of the prosthesis 100 and/or another component of any system disclosed herein that is configured to execute that functionality or otherwise have a functionality or otherwise to execute that method action.

Any action disclosed herein that is executed by a component of any system disclosed herein can be executed by the device 240 and/or the prosthesis 100 in an alternative embodiment, unless otherwise noted or unless the art does not enable such. Thus, any functionality of a component of the systems detailed herein can be present in the device 240 and/or the prosthesis 100 as alternative embodiment. Thus, any disclosure of a functionality of a component herein corresponds to structure of the device 240 and/or the prosthesis 100 that is configured to execute that functionality or otherwise have a functionality or otherwise to execute that method action.

It is further noted that any disclosure of a device and/or system detailed herein also corresponds to a disclosure of otherwise providing that device and/or system.

It is also noted that any disclosure herein of any process of manufacturing other providing a device corresponds to a device and/or system that results therefrom. Is also noted that any disclosure herein of any device and/or system corresponds to a disclosure of a method of producing or otherwise providing or otherwise making such.

Any embodiment or any feature disclosed herein can be combined with any one or more or other embodiments and/or other features disclosed herein, unless explicitly indicated and/or unless the art does not enable such. Any embodiment or any feature disclosed herein can be explicitly excluded from use with any one or more other embodiments and/or other features disclosed herein, unless explicitly indicated that such is combined and/or unless the art does not enable such exclusion.

While various embodiments of the present invention have been described above, it should be understood that they have been presented by way of example only, and not limitation. It will be apparent to persons skilled in the relevant art that various changes in form and detail can be made therein without departing from the spirit and scope of the invention.

What is claimed is:

1. A method of at least partially fitting a hearing prosthesis device to a recipient, comprising:
   obtaining access to a sensory prosthesis that has been used to evoke a sensory percept using a first focusing regime for a temporal period corresponding to at least acclimation to the first focusing regime; and
   adjusting a control setting of the prosthesis to increase focusing relative to that which is the case with respect to the first focusing regime, wherein
   the action of adjusting the control setting includes purposely adjusting the control setting to have focusing that is effectively less focused than a maximum focus possible.

2. The method of claim 1, wherein:
   the first focusing regime is monopolar stimulation; and
   the action of adjusting the control setting includes implementing a second focusing regime that is tripolar stimulation and/or partial tripolar and/or multipolar stimulation.

3. The method of claim 1, wherein:
   the first focusing regime is one of monopolar stimulation, bipolar stimulation, tripolar or partial tripolar stimulation; and
   the action of adjusting the control setting includes implementing a second focusing regime that is a focused multipolar regime.

4. The method of claim 1, further comprising:
   fine tuning threshold and comfort levels for the adjusted control setting.

5. The method of claim 1, further comprising:
   obtaining second access to the sensory prosthesis after the sensory prosthesis has been used to evoke sensory percepts using the adjusted control setting for a second temporal period corresponding to at least acclimation to the adjusted control setting; and
   adjusting a control setting of the prosthesis a second time to increase focusing relative to that which is the case with respect to the focusing of the adjusted control settings for the second temporal period, wherein
   the action of adjusting the control setting a second time includes purposely adjusting the control setting to have focusing that is effectively less focused than a maximum focus possible.

6. The method of claim 1, further comprising:
   a first action of obtaining nth access to the sensory prosthesis after the sensory prosthesis has been used to evoke sensory percepts using the adjusted control setting for an nth temporal period corresponding to at least acclimation to the first focusing regime; and
   a first adjusting a control setting of the prosthesis an nth time to increase focusing relative to that which is the case with respect to the focusing of the adjusted control settings for the nth temporal period, wherein the action of adjusting the control setting the nth time includes purposely adjusting the control setting to have focusing that is effectively less focused than a maximum focus possible; and repeating the first action and the first adjusting for n equals at least 10.

7. The method of claim 1, further comprising:
fine tuning threshold and comfort levels for the adjusted control setting, where the action of fine tuning is executed by the recipient of the prosthesis without at least active involvement of a sensory professional.

8. A non-transitory computer-readable media having recorded thereon, a computer program for executing at least a portion of a method of fitting a sensory prosthesis to a recipient, the computer program including:
code for enabling recipient controlled gradual transitioning of the prosthesis from less focused stimulation to more focused stimulation.

9. The media of claim 8, further comprising:
code for adjusting stimulation intensity levels based on input from the recipient for given focusing regimes.

10. The media of claim 8, further comprising:
code for enabling recipient adjusting a map and/or developing a new map for respective focusing settings of the prosthesis.

11. The media of claim 8, further comprising:
code for obtaining data indicative of recipient perceptions for respective prosthesis focusing regimes.

12. The media of claim 8, wherein:
the code for enabling the recipient-controlled transitioning is code for self-fitting of the prosthesis to the recipient; and
the code for self-fitting includes code for adjusting stimulation magnitudes of channels after the channels are focused.

13. The media of claim 8, further comprising:
code for evaluating an efficacy of results of the gradual transitioning; and
code for executing supplemental focusing and/or defocusing based on the evaluation of the efficacy.

14. A method, comprising:
adjusting and/or changing control settings of a sensory prosthesis in an incremental manner, wherein
the action of adjusting and/or changing the control settings in the incremental manner reduces the risk of overstimulation of the recipient relative to that which would be the case in the absence of the limitation of the incremental manner.

15. The method of claim 14, wherein:
the incremental manner includes focusing the prosthesis to have more focus than that which was previously the case but less focus than a maximum focus possible by the prosthesis.

16. The method of claim 14, further comprising:
obtaining data indicative of an efficacy of the adjusted and/or changed control setting; and
further adjusting and/or changing the control setting based on the obtained data for remedial purposes.

17. The method of claim 14, wherein:
the action of adjusting and/or changing is executed entirely by a recipient of the prostheses.

18. The method of claim 14, wherein:
the method is executed using a body carried smart device that is in communication with a hearing prosthesis, wherein the prosthesis is a hearing prosthesis.

19. The method of claim 14, wherein:
the action of adjusting and/or changing control settings of a sensory prosthesis in an incremental manner is executed at least ten times by the recipient, whether or not such is serial.

20. The method of claim 14, wherein:
the prosthesis has at least five stimulation channels;
the action of adjusting and/or changing the control settings in the incremental manner includes adjusting a stimulation of at least most of the stimulation channels;
the method includes adjusting a magnitude of stimulation of at least most of the stimulation channels after adjusting and/or changing the control settings so that a perceived magnitude of a real-world stimulus having a magnitude is at least effectively the same across the at least most of the stimulation channels.

* * * * *